United States Patent [19]

Sato et al.

[11] Patent Number: 5,712,403
[45] Date of Patent: Jan. 27, 1998

[54] PHOSPHONITE COMPOUNDS AND THEIR COMPLEXES

[75] Inventors: Keiichi Sato; Yoko Seto; Iwao Nakajima, all of Yokohama, Japan

[73] Assignee: Mitsubishi Chemical Corporation, Tokyo, Japan

[21] Appl. No.: 727,042

[22] Filed: Oct. 8, 1996

Related U.S. Application Data

[62] Division of Ser. No. 475,619, Jun. 7, 1995, Pat. No. 5,600,032.

Foreign Application Priority Data

May 29, 1994 [JP] Japan ................................ 6-147732

[51] Int. Cl.$^6$ ........................ C07F 9/02; C07F 15/00
[52] U.S. Cl. ................ 556/19; 556/136; 502/162; 568/14; 568/17
[58] Field of Search .............. 556/136, 19; 568/14, 568/17; 502/162

[56] References Cited

U.S. PATENT DOCUMENTS

| | | | |
|---|---|---|---|
| 5,210,243 | 5/1993 | Kolich | 556/18 |
| 5,530,150 | 6/1996 | Takaya et al. | 556/18 |
| 5,543,536 | 8/1996 | Tam | 556/13 |
| 5,545,769 | 8/1996 | Baker et al. | 570/134 |

*Primary Examiner*—Porfirio Nazario-Gonzalez
*Attorney, Agent, or Firm*—Oblon, Spivak, McClelland, Maier & Neustadt, P.C.

[57] ABSTRACT

A method for producing an unsaturated alcohol having a chain structure formed by oligomerization of a conjugated alkadiene, which comprises reacting a conjugated alkadiene and water in the presence of carbon dioxide by means of a palladium compound and a phosphorus compound having at least one trivalent phosphorus-oxygen single bond, as catalyst.

10 Claims, 9 Drawing Sheets

PHOSPHONITE COMPOUNDS AND THEIR COMPLEXES

This is a Continuation of application Ser. No. 08/475,619 filed on Jun. 7, 1995, now U.S. Pat. No. 5,600,032.

BACKGROUND OF THE INVENTION

FIELD OF THE INVENTION

The present invention relates to a method for producing an unsaturated alcohol. More particularly, the present invention relates to a method for producing an unsaturated alcohol which is a hydrated oligomer of a conjugated alkadiene, which comprises reacting a conjugated alkadiene and water in the presence of carbon dioxide by means of a palladium compound and a phosphorus compound having at least one trivalent phosphorus-oxygen single bond, as catalyst. Further, the present invention relates to a novel palladium complex, a phosphonite compound, and a method for producing a saturated alcohol useful, for example, as a starting material for preparation of various organic compounds for special uses, which comprises hydrogenating the unsaturated alcohol obtained by the method of the present invention.

DISCUSSION OF BACKGROUND

Unsaturated alcohols, particularly octadienols including octa-2,7-dien-1-ol, are compounds important for chemical industry as intermediates useful for producing n-octanol or its esters.

As a method for producing such unsaturated alcohols, a method is known which comprises reacting conjugated alkadienes and water in the presence of carbon dioxide by means of a palladium compound and a phosphine compound as catalyst, to produce alkadienols as hydrated dimers, for example, from Chemical Communications 330 (1971) and Japanese Examined Patent Publication No. 10565/1975. In such a case, as a phosphine compound used as a ligand of the palladium catalyst, a triaryl phosphine is known to be advantageous. However, in this case, further improvements are desired in the yield of alkadienols and in the selectivity for the desired octa-2,7-dien-1-ol.

SUMMARY OF THE INVENTION

In a complex catalyst reaction, the metal component used as a catalyst plays an important role. At the same time, selection of the type of the ligand used in combination therewith gives a substantial influence over the activity and the selectivity of the catalyst reaction. The present inventors have conducted extensive studies to provide an industrially advantageous method for producing unsaturated alcohols, whereby a desired unsaturated alcohol can be obtained in good yield under high selectivity in the reaction of a conjugated alkadiene and water by means of a palladium compound and a phosphorus compound, as catalyst.

It is an object of the present invention to provide a method for producing an unsaturated alcohol having a structure formed by oligomerization of a conjugated diene, which comprises reacting a conjugated alkadiene and water by means of a novel catalyst system.

The present inventors have surprisingly found that by reacting a conjugated alkadiene and water in the presence of carbon dioxide by means of a catalyst consisting of a combination of a palladium compound and a phosphorus compound having at least one trivalent phosphorus-oxygen single bond (i.e., single bond between a trivalent phosphorus atom and an oxygen atom), instead of a combination of a palladium compound and a phosphine compound, which has been known to be useful as a catalyst, the catalyst component can be effectively and efficiently utilized even at a low palladium concentration, and an unsaturated alcohol having a chain structure (i.e., skeleton) formed by oligomerization of the conjugated diene, specifically octa-2,7-dien-1-ol in the case where 1,3-butadiene is used as the conjugated alkadiene, can be obtained highly selectively in good yield. Further, they have found that when a reaction is carried out by using such starting materials, it is possible to synthesize novel 6-vinyl-2,8,13-tetradecatrien-1-ol which is useful as a synthetic starting material for an organic chemical reaction.

Thus, the present invention provides a method for producing an unsaturated alcohol having a chain structure formed by oligomerization of a conjugated alkadiene, which comprises reacting a conjugated alkadiene and water in the presence of carbon dioxide by means of a palladium compound and a phosphorus compound having at least one trivalent phosphorus-oxygen single bond, as catalyst.

The present invention also provides 6-vinyl-2,8,13-tetradecatrien-1-ol as a novel compound.

Further, the present invention provides novel phosphonite compounds of the formulas (7) and (8):

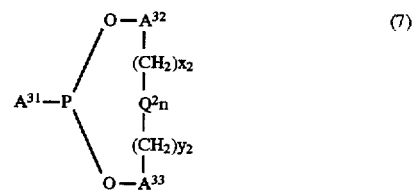

wherein $A^{31}$ is an aryl group or an alkyl group, which may be substituted, provided that the alkyl groups has no branch at the β-position, each of $A^{32}$ and $A^{33}$ is an arylene group having an alkyl substituent and $A^{32}$ and $A^{33}$ are not the same, each of $x^2$ and $y^2$ which are independent of each other, is an integer of 0 or 1, $Q^2$ is a bivalent linking group of the formula $-CR^{41}R^{42}-$, $-O-$, $-S-$, $SO_2-$, $-NR^{43}-$, $-SiR^{44}R^{45}-$ or $-CO-$, each of $R^{41}$ and $R^{42}$ which are independent of each other, is hydrogen, a $C_{1-12}$ alkyl group, a phenyl group, a tolyl group or an anisyl group, and each of $R^{43}$, $R^{44}$ and $R^{45}$ which are independent of one another, is hydrogen or a methyl group, and n is an integer of from 0 to 1;

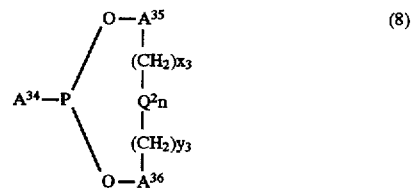

wherein $A^{34}$ is an alkyl group or an aralkyl group, which has a branch at the β-position, each of $A^{35}$ and $A^{36}$ which are independent of each other, is an arylene group which may be substituted, each of $x^3$ and $y^3$ which are independent of each other, is an integer of 0 or 1, $Q^2$ is a bivalent linking group of the formula $-CR^{46}R^{47}-$, $-O-$, $-S-$, $-SO_2-$, $-NR^{48}-$, $-SiR^{49}R^{50}-$ or $-CO-$, each of $R^{46}$ and $R^{47}$ which are independent of each other, is hydrogen, a $C_{1-12}$ alkyl group, a phenyl group, a tolyl group or an anisyl group, each of $R^{48}$, $R^{49}$ and $R^{50}$ which are independent of one another, is hydrogen or a methyl group, and n is an integer of 0 or 1.

Still further, the present invention provides a method for producing a saturated alcohol, which comprises reacting a conjugated alkadiene and water in the presence of carbon dioxide by means of a palladium compound and a phosphorus compound having at least one trivalent phosphorus-oxygen single bond, as catalyst, to obtain an unsaturated alcohol having a structure formed by oligomerization of the conjugated alkadiene, and then hydrogenating this unsaturated alcohol to obtain the corresponding saturated alcohol.

DESCRIPTION OF THE PREFERRED EMBODIMENTS

Figure 1:
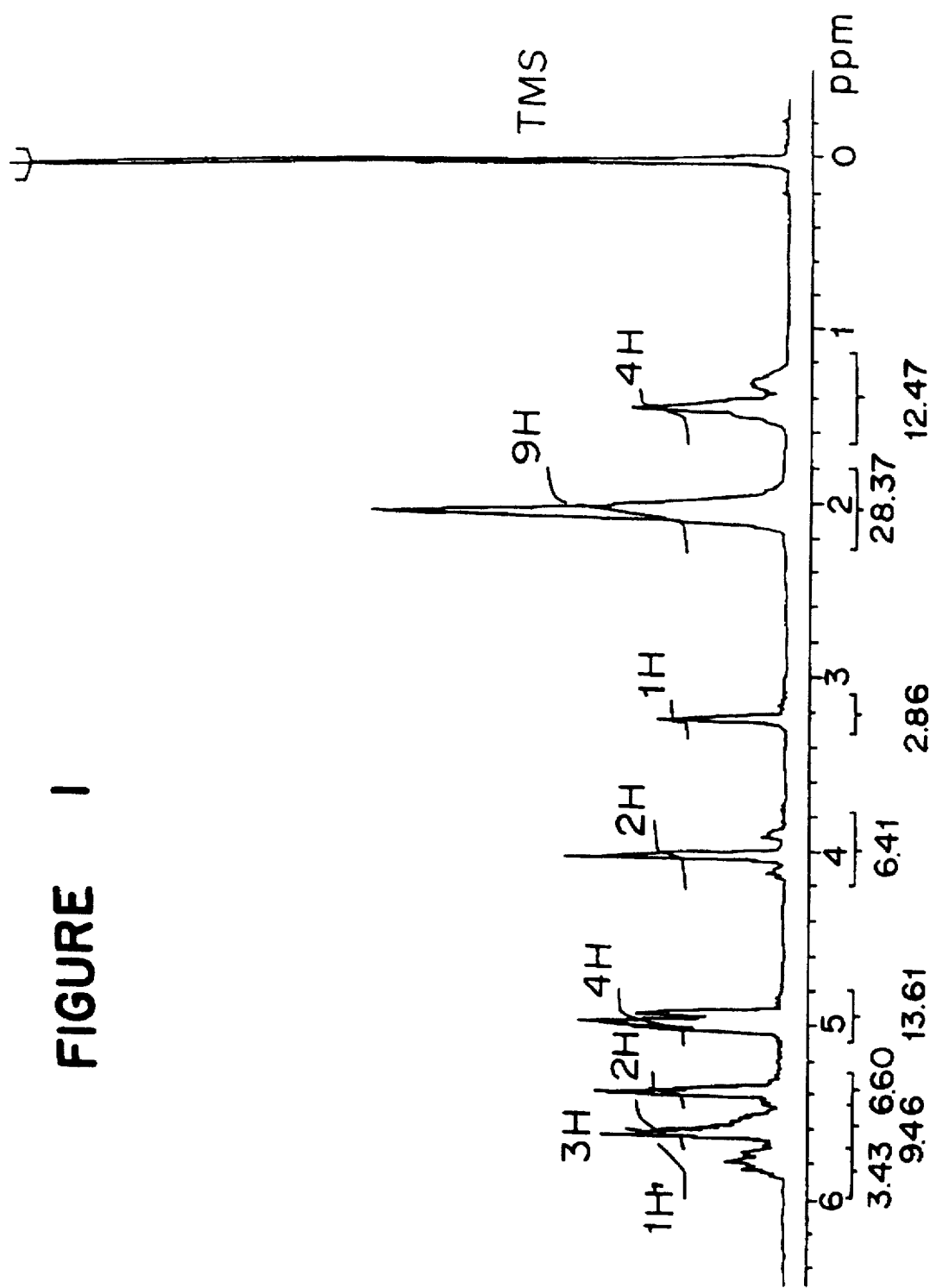
FIG. 1 shows a $^1$H-NMR spectrum of the high boiling point compound obtained in Example 1.

Now, the present invention will be described in detail with reference to the preferred embodiments.

The conjugated alkadiene to be reacted with water to produce an unsaturated alcohol by the method of the present invention may, for example, be 1,3-butadiene, 2-ethyl-1,3-butadiene, 2,3-dimethyl-1,3-butadiene, isoprene, 1,3-pentadiene, chloroprene or 1,3-octadiene. In the case of 1,3-butadiene, the raw material which is usually available, is purified 1,3-butadiene or so-called BBP, i.e. a mixture of $C_4$ fraction from the decomposition product of naphtha.

When BBP is used as the raw material taking mainly the economical advantage into consideration, it is advisable to preliminarily separate and remove acetylenes and allenes contained in the raw material BBP. The method for reducing acetylenes and allenes is not particularly limited, and various known methods may suitably be employed. In a case where octadienols or hexadecatetraenols are to be produced by even number oligomerization and hydration (such as dimerization and hydration or tetramerization and hydration) of 1,3-butadiene, the total concentration of acetylenes and allenes in the 1,3-butadiene raw material after removal or reduction of acetylenes and allenes in BBP, is desired to be as low as possible, usually at a level of not more than 1.0 wt %, relative to 1,3-butadiene.

On the other hand, as the water, as the other raw material, pure water not to be influential over the even number oligomerization and hydration reaction is suitably employed. The amount of the water is not particularly limited, and it is usually selected within a range of from 0.5 to 10 mols, preferably from 1 to 5 mols, per mol of the conjugated alkadiene.

In the present invention, a palladium compound is used as a main catalyst. The form and the valency of the palladium compound to be used is not particularly limited, and a zerovalent or bivalent compound may be used. Specifically, it may, for example, be a bivalent palladium compound, e.g. a palladium salt of an inorganic acid such as palladium nitrate; a palladium salt of an organic acid, such as palladium acetate; or a bivalent palladium complex such as bis(actylacetone)palladium or bis(tributylphosphine)palladium acetate, or a zerovalent palladium complex such as tetrakis (triphenylphosphine)palladium, tris(dibenzylideneacetone) dipalladium, or (1,5-cyclooctadiene)(maleic anhydride) palladium. However, most preferred is a palladium complex having, as the sole ligand, a trivalent phosphorus compound having at least one phosphorus-oxygen single bond, which is used as a co-catalyst. If a palladium compound having a ligand other than a phosphorus compound, is used, useless by-products will be formed by the reaction of the ligand with the starting material alkadiene, and the starting material alkadiene will be consumed uselessly. Whereas, when the palladium complex having, as the sole ligand, a trivalent phosphorus compound having at least one phosphorus-oxygen single bond, is used, such an undesirable phenomenon will not occur, and the starting material alkadiene can be consumed effectively and efficiently. Specific examples of such a palladium complex include a bis(phosphinite) palladium complex, a tris(phosphinite)palladium complex, a tetrakis(phosphinite)palladium complex, a bis(phosphonite) palladium complex, a tris(phosphonite)palladium complex, a tetrakis(phosphonite)palladium complex, a bis(phosphite) palladium complex, a tris(phosphite)palladium complex, and a tetrakis(phosphite)palladium complex.

The amount of such a palladium compound may be varied within a wide range. However, it is usually selected within a range of from 0.000002 to 1 g atom, preferably from 0.00002 to 0.1 g atom, as palladium per mol of the conjugated alkadiene.

It is a feature of the present invention to use a phosphorus compound having at least one trivalent phosphorus-oxygen single bond as a cocatalyst.

Phosphorus compounds having at least one trivalent phosphorus-oxygen single bond may be classified into three types depending upon the number of trivalent phosphorus-oxygen bonds i.e. a phosphinite (a phosphorus compound having a structure in which one oxygen atom and two carbon atoms are bonded to a phosphorus atom by single bonds, respectively), a phosphonite (a phosphorus compound having a structure wherein two oxygen atoms and one carbon atom are bonded to a phosphorus atom by single bonds respectively) and phosphite (a phosphorus compound having a structure wherein three oxygen atoms are bonded to a phosphorus atom by single bonds respectively).

As the phosphonite compound useful as a cocatalyst, a phosphonite compound of the following formula (1), (2), (3) or (4) may specifically be mentioned:

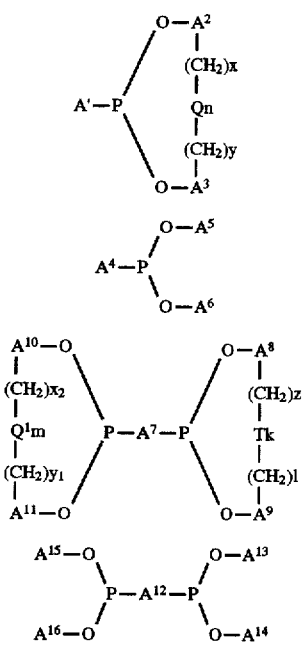

(1)

(2)

(3)

(4)

In the formulas (1) to (4), each of $A^1$ and $A^4$ which are independent of each other, is an aryl group or an alkyl group, which may be substituted, each of $A^5$, $A^6$, $A^{13}$, $A^{14}$, $A^{15}$ and $A^{16}$ which are independent of one another, is an aryl group which may be substituted, each of $A^2$, $A^3$, $A^8$, $A^9$, $A^{10}$ and $A^{11}$ which are independent of one another, is an arylene group which may be substituted, each of $A^7$ and $A^{12}$ which are independent of one another, is a bivalent hydrocarbon group which may be substituted, each of x, $x^1$, y, $y^1$, z and l which are independent of one another is an integer of 0 or 1, each of Q, $Q^1$ and T which are independent of one another, is a bivalent linking group of the formula —$CR^1R^2$—, —O—, —S—, —$SO_2$—, —$NR^3$—, —$SiR^4R^5$— or —CO—, each of $R^1$ and $R^2$ which are independent of each other, is hydrogen, a $C_{1-12}$ alkyl group, a phenyl group, a tolyl group or an anisyl group, each of $R^3$, $R^4$ and $R^5$ which are independent of one another, is hydrogen or a methyl group, and n is an integer of 0 or 1.

In the formulas (1) to (4), each of $A^1$ and $A^4$ may be a $C_{6-30}$ alkyl group, for example, an alkyl group such as a methyl group, an ethyl group, a propyl group, a butyl group or an octyl group, or an aryl-substituted alkyl group such as a benzyl group. Such an alkyl group may be substituted by e.g. a $C_{1-20}$ alkoxy group such as a methoxy group, an ethoxy group, a hexyloxy group or a decyloxy group, a $C_{2-30}$ dialkylamino group such as a dimethylamino group or a dioctylamino group, or a group of the formula —$SO_3Na$, —COONa or —$COOCH_3$. The aryl group for $A^1$, $A^4$, $A^5$, $A^6$, $A^{10}$, $A^{11}$, $A^{13}$, $A^{14}$, $A^{15}$ and $A^{16}$ may be a $C_{6-30}$ aryl group such as a phenyl group, a naphthyl group, a tolyl group, a xylyl group or an alkyl-substituted naphthyl group. Such an aryl group may be substituted by e.g. a $C_{1-20}$ alkoxy group such as a methoxy group, an ethoxy group, a hexyloxy group or a decyloxy group, a $C_{2-30}$ dialkylamino group such as a dimethylamino group or a dioctylamino group, or a group of the formula —$SO_3Na$, —COONa or —$COOCH_3$. The arylene group for $A^2$, $A^3$, $A^8$, $A^9$, $A^{10}$ and $A^{11}$ may be a $C_{6-30}$ arylene group such as a phenylene group, an alkyl-substituted phenylene group, an aryl-substituted phenylene group, a naphthylene group, an alkyl-substituted naphthylene group or an aryl-substituted naphthylene group. Such an arylene group may be substituted by e.g. a $C_{1-20}$ alkoxy group such as a methoxy group, an ethoxy group, a hexyloxy group or a decyloxy group, a $C_{2-30}$ dialkylamino group such as a dimethylamino group or a dioctylamino group, or a group of the formula —$SO_3Na$, —COONa or —$COOCH_3$. The bivalent hydrocarbon group for $A^7$ and $A^{12}$ may be a $C_{6-30}$ arylene group such as a phenylene group, an alkyl-substituted phenylene group, an aryl-substituted phenylene group, a naphthylene group, an alkyl-substituted naphthylene group or an aryl-substituted naphthylene group, a $C_{6-30}$ alkylene group such as a methylene group, an ethylene group, a butylene group, a hexamethylene group, or an aryl-substituted butylene group, or a group wherein the above alkylene group and the arylene group are bonded in series. Such a bivalent hydrocarbon group may be substituted by e.g. a $C_{1-20}$ alkoxy group such as a methoxy group, an ethoxy group, a hexyloxy group or a decyloxy group, a $C_{2-30}$ dialkylamino group such as dimethylamino group or a dioctylamino group, or a group of the formula —$SO_3Na$, —COONa or —$COOCH_3$. The $C_{1-12}$ alkyl group for $R^1$ and $R^2$ may, for example, be a methyl group, an ethyl group, a butyl group, a hexyl group, an octyl group or a decyl group.

Specific examples of such a phosphonite compound include the following compounds:

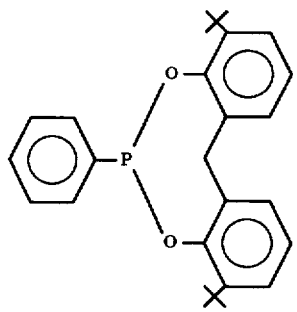 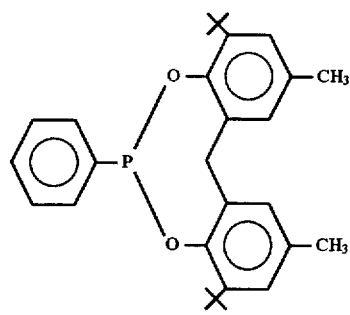 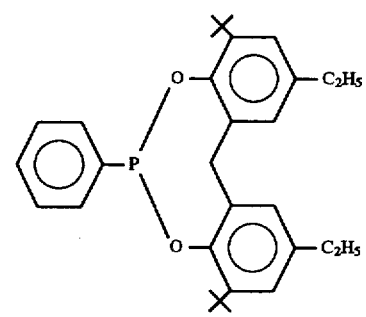

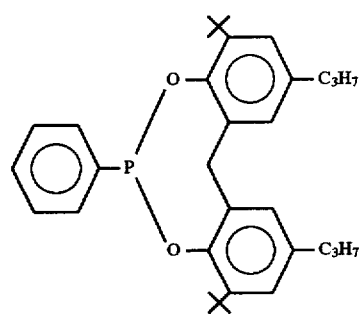
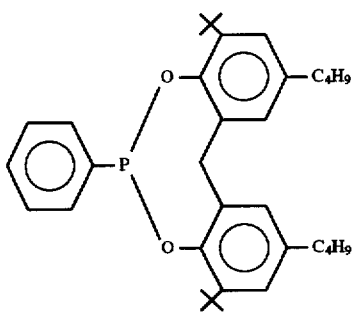
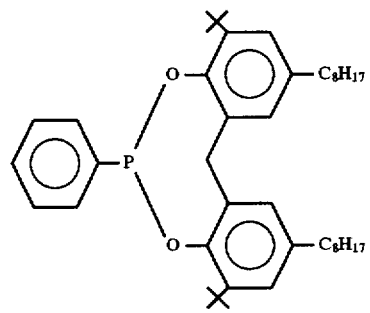
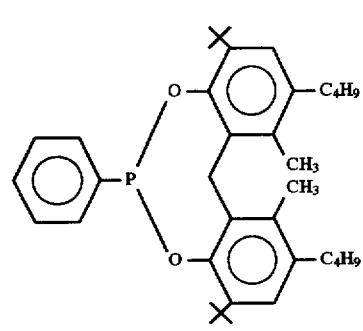
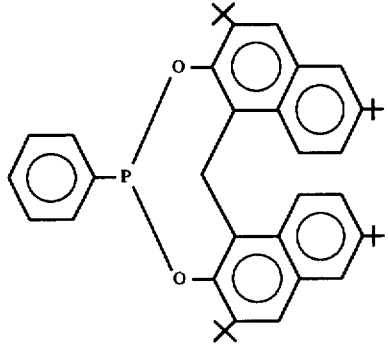
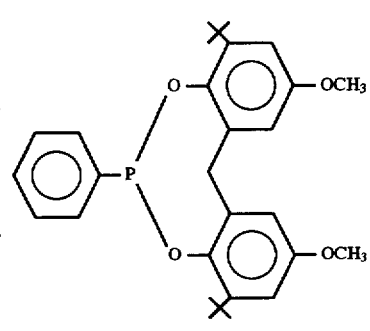
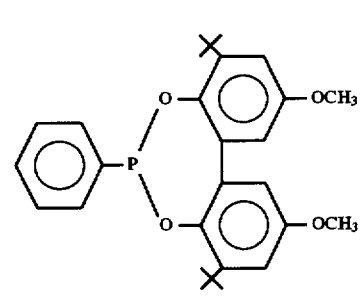
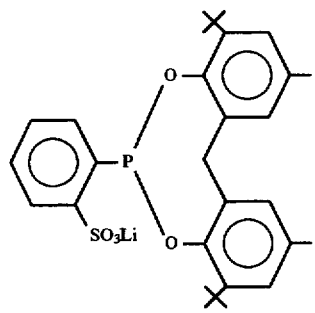
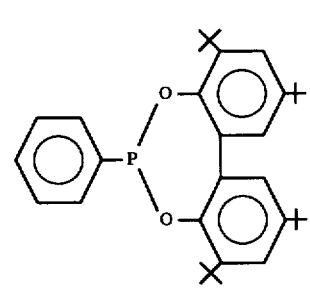
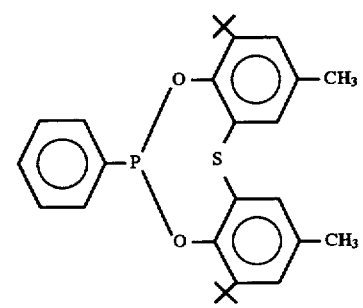
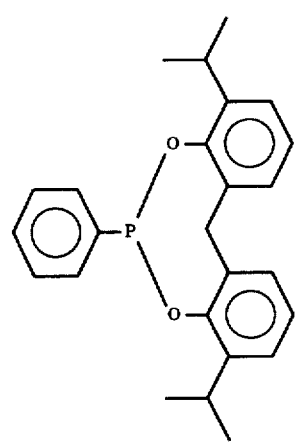
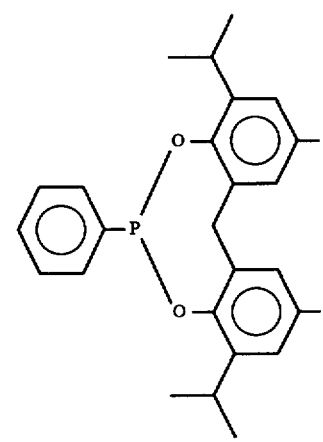

-continued
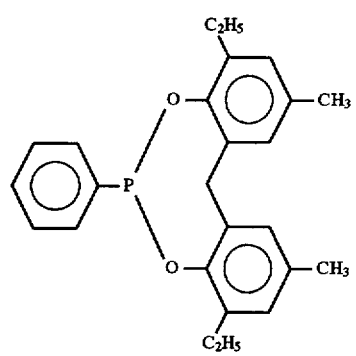
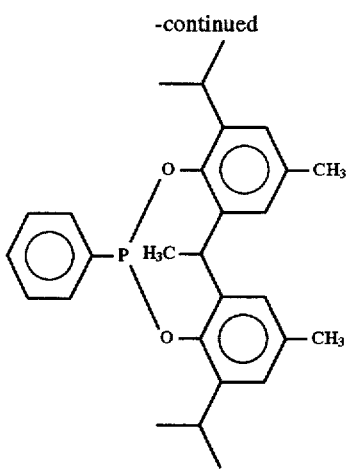
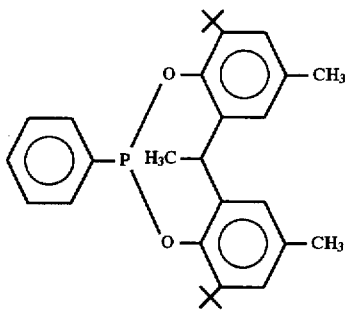
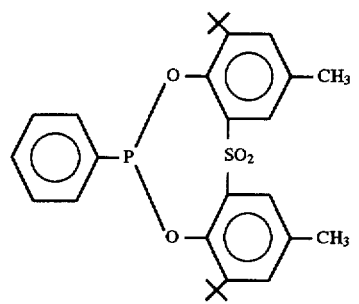
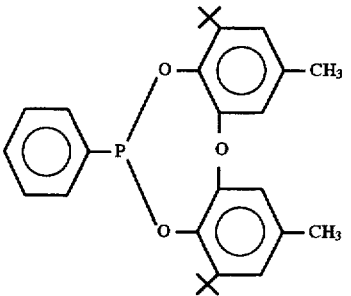
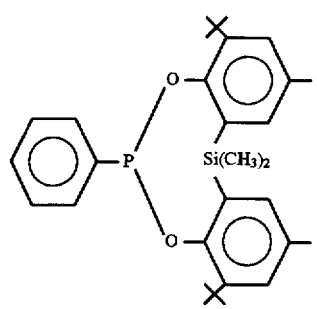
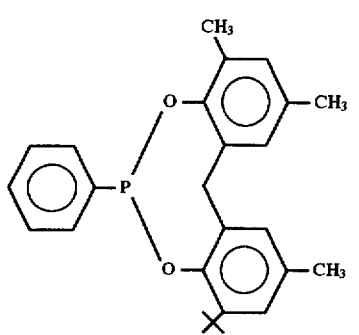
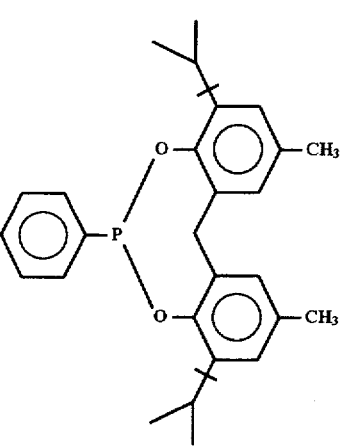
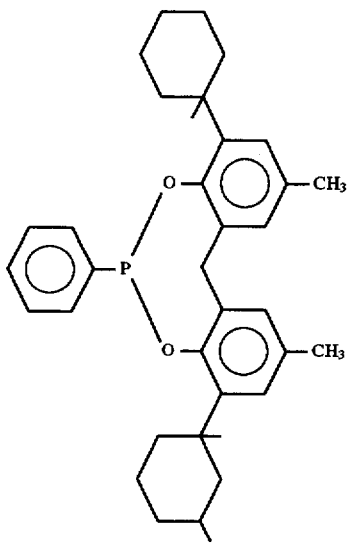
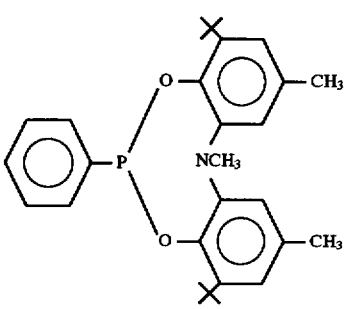
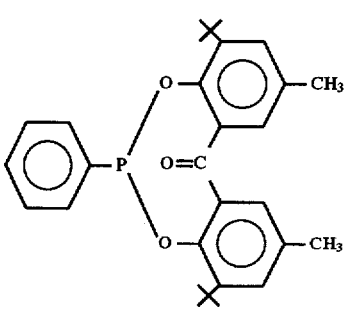
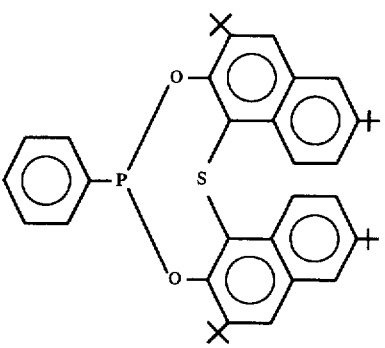

-continued
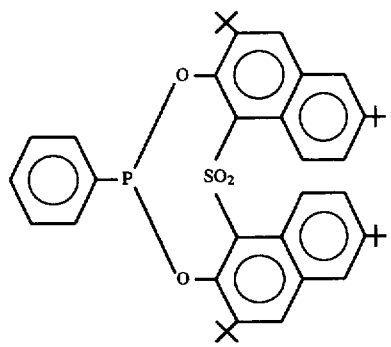
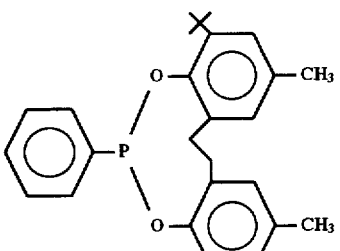
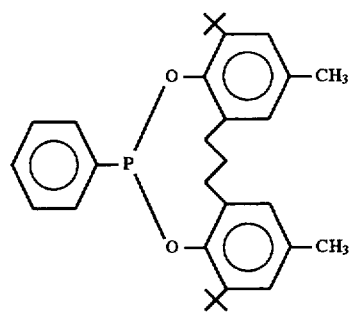
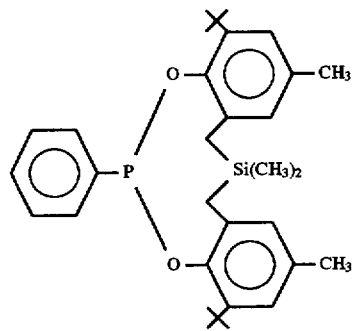
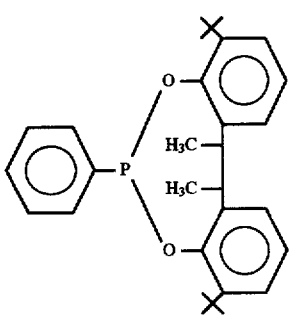
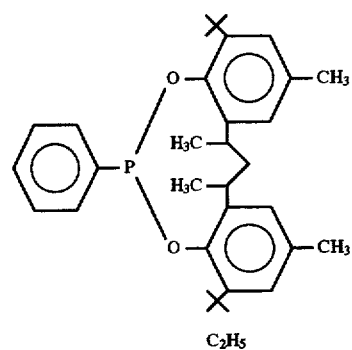
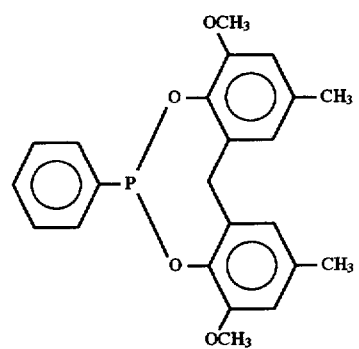
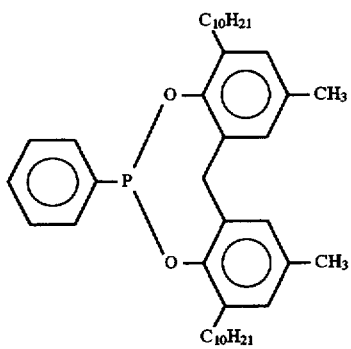
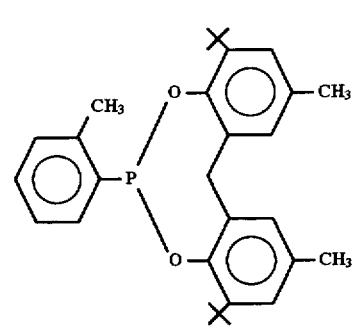
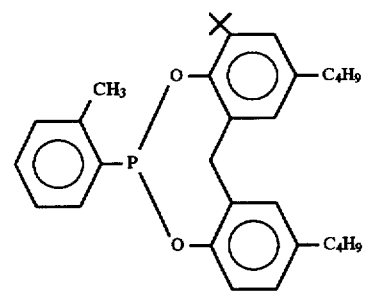
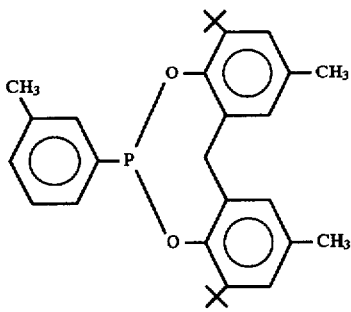
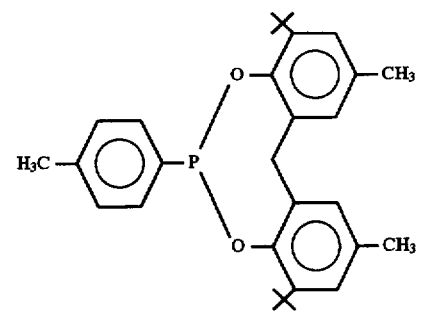
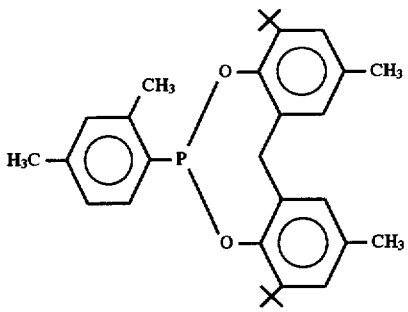

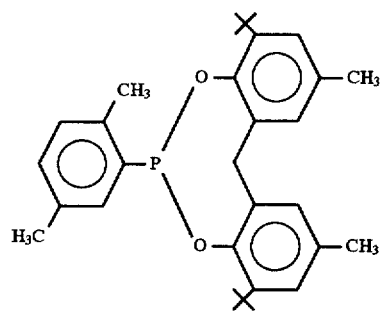
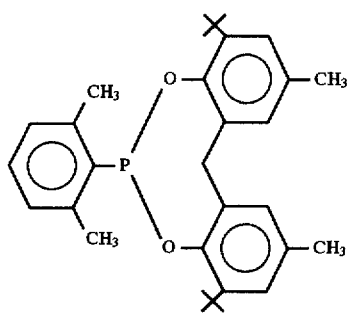
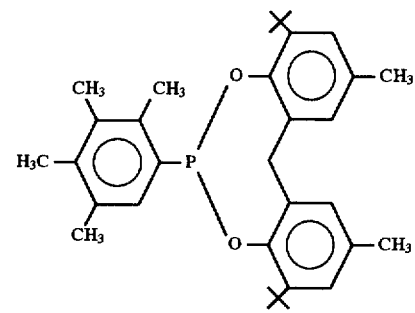
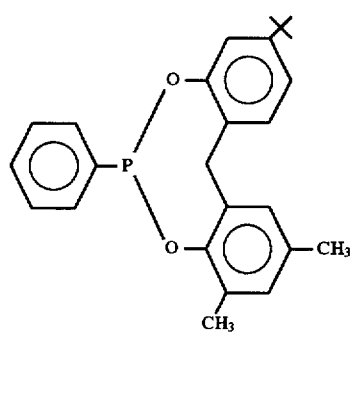
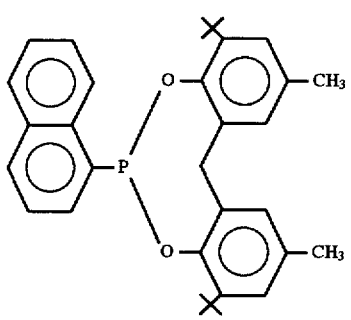
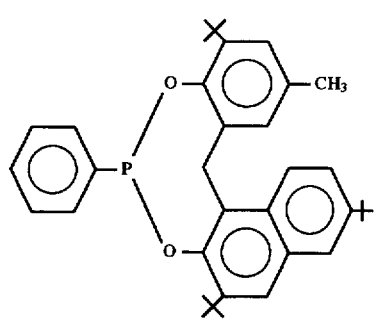
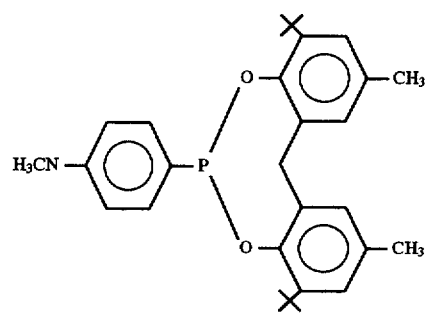
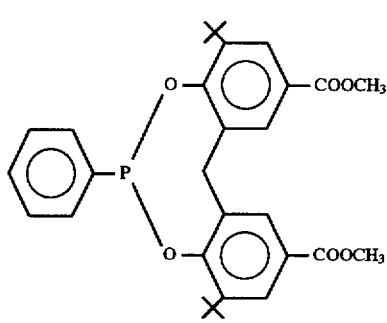
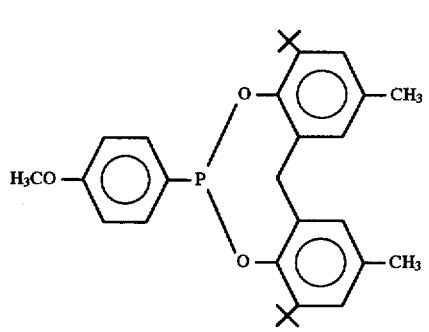
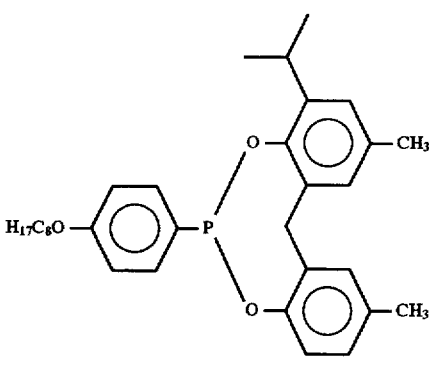

-continued
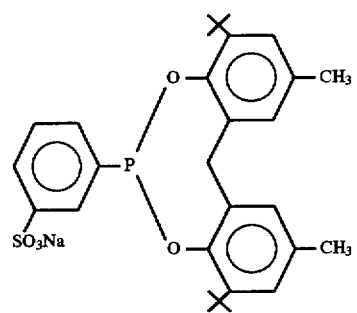
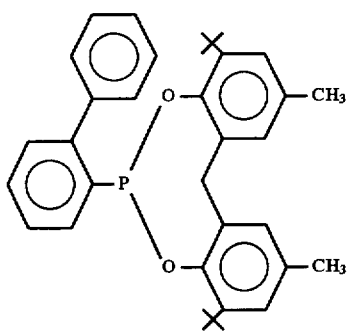
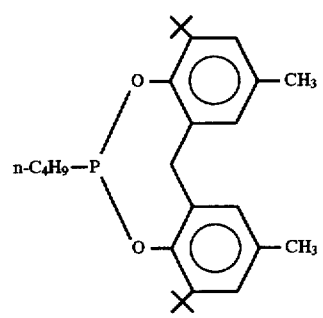
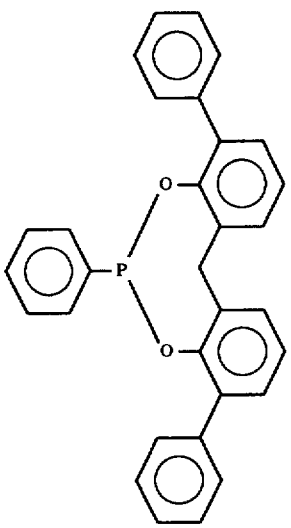
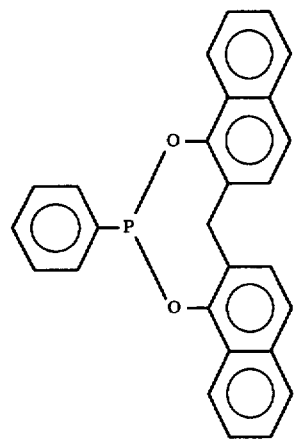
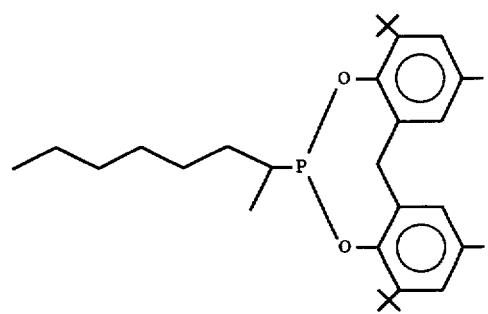
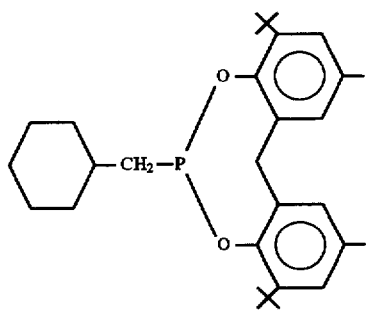
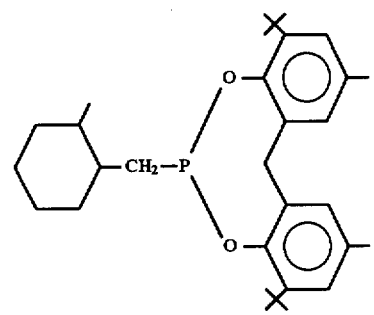
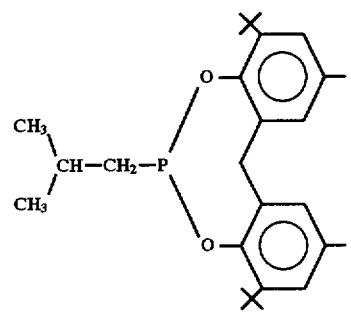
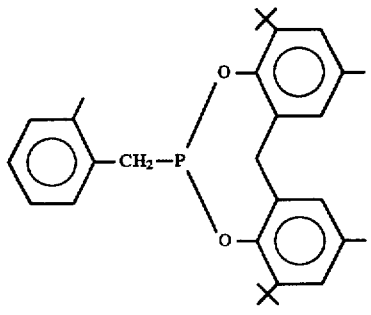

-continued
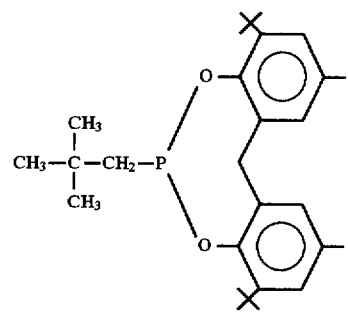
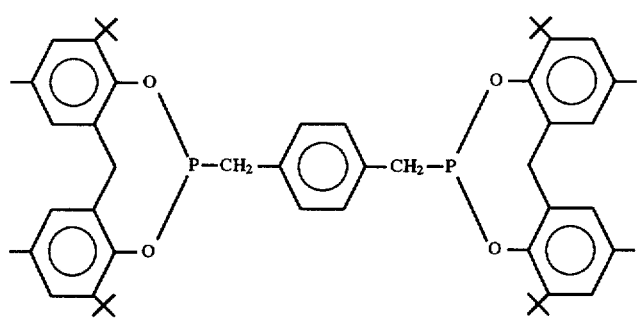
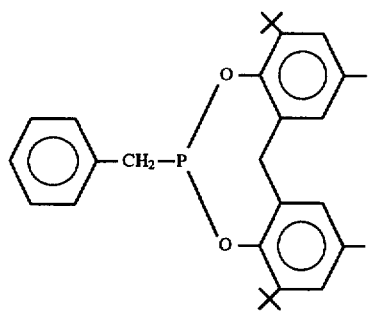
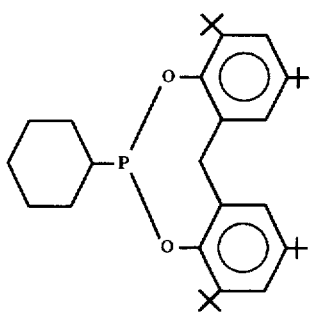
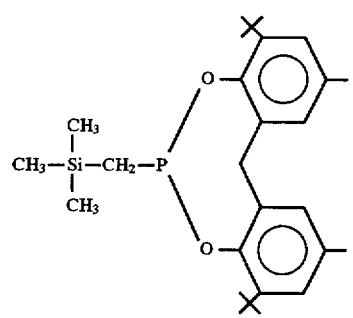
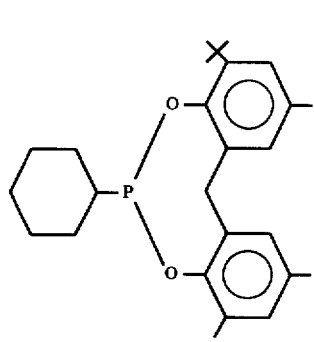
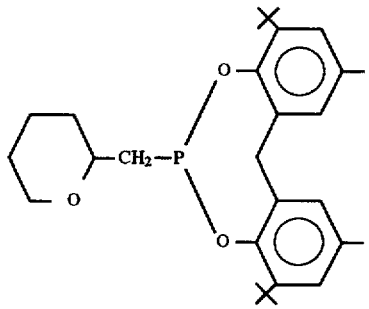
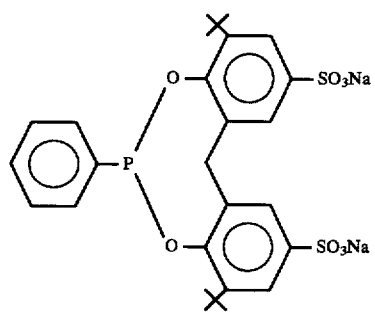
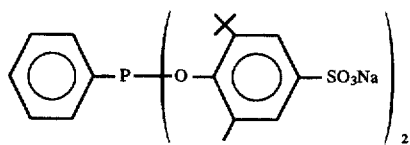

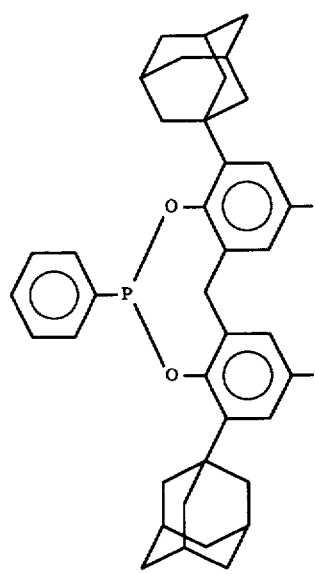
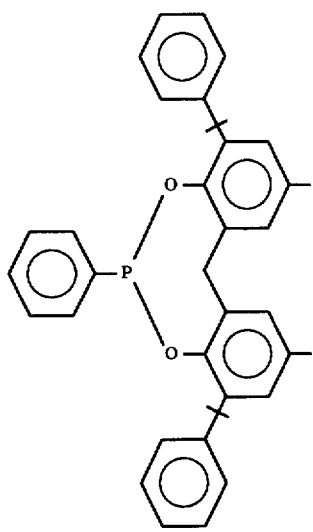
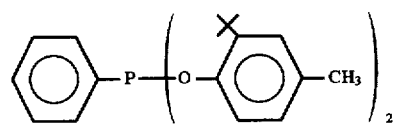
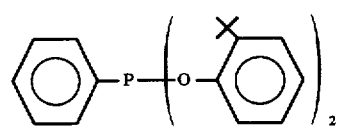
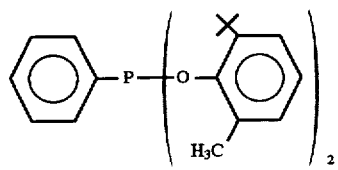
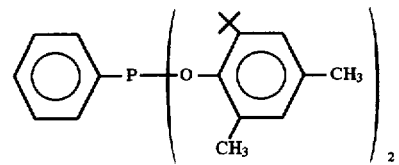
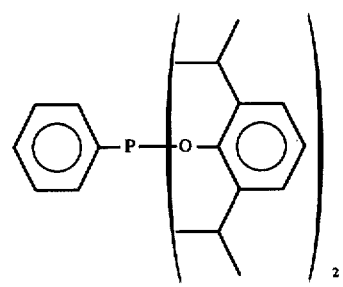
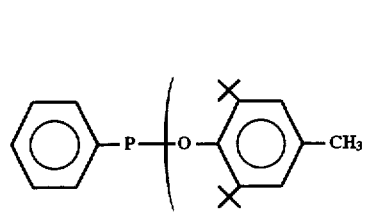
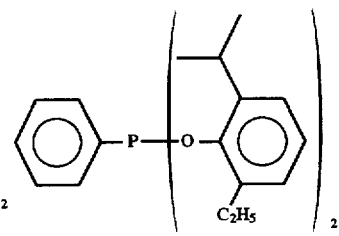
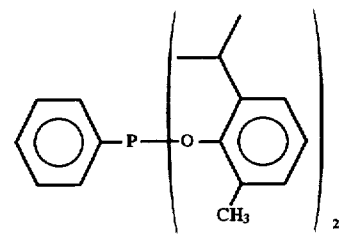
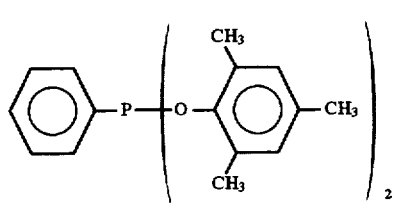
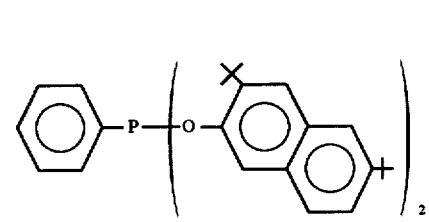
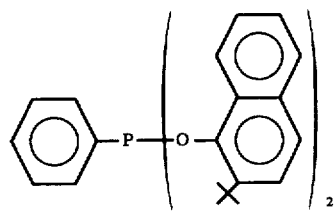

-continued
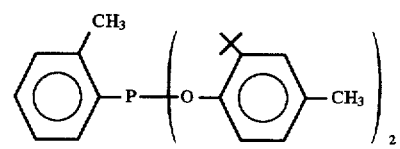 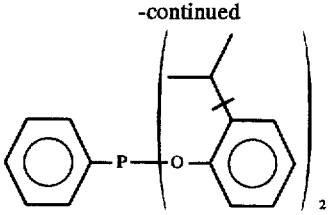 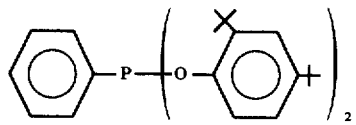
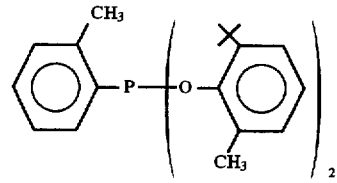 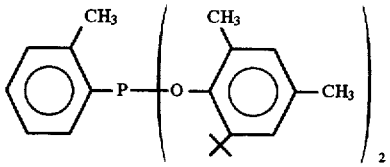
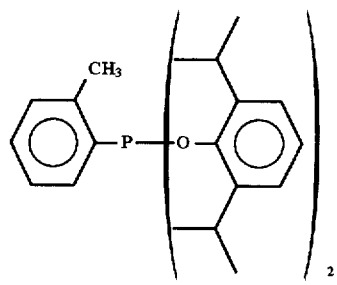 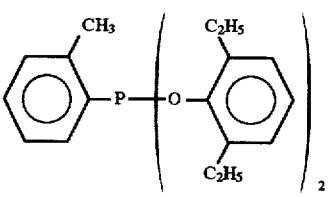
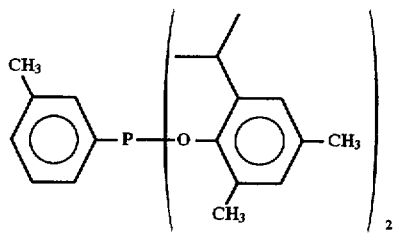 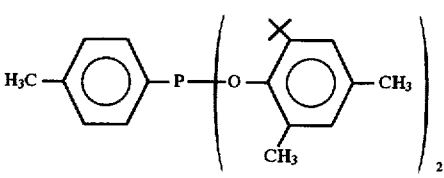
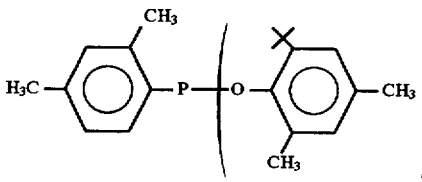 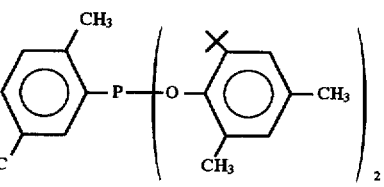
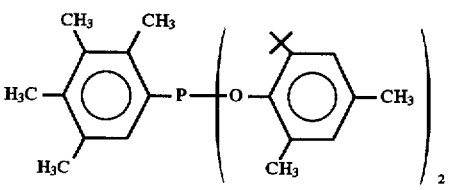 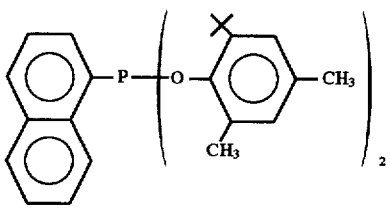
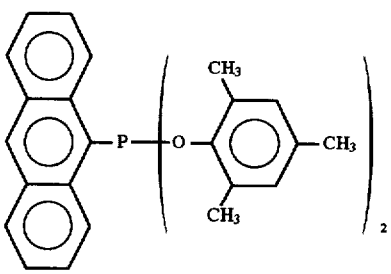 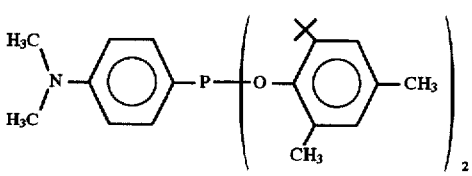

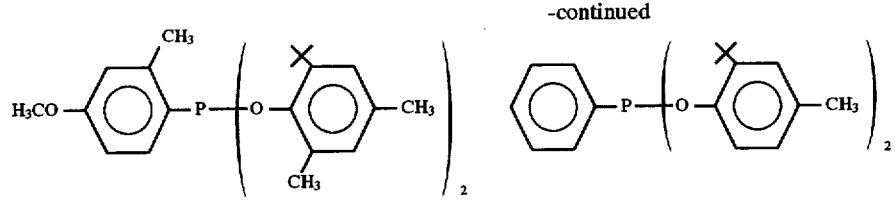
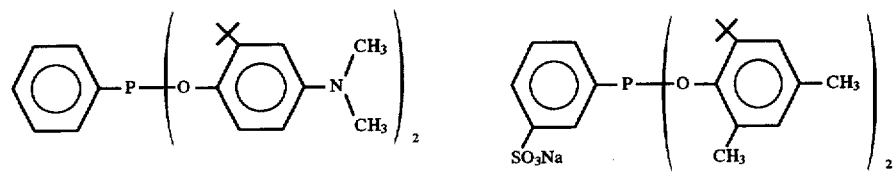
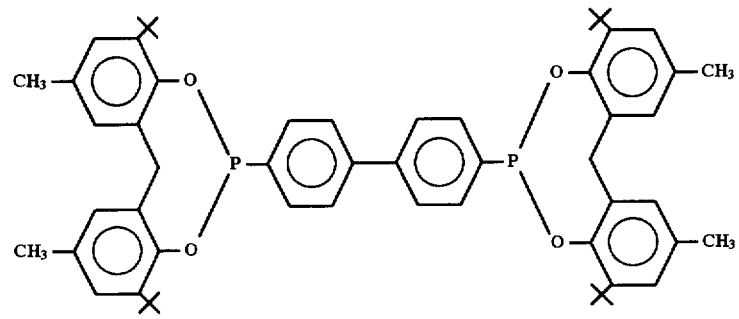
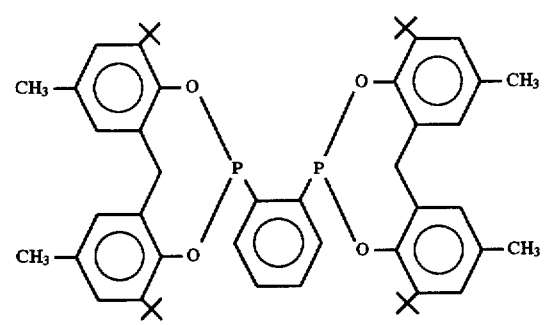
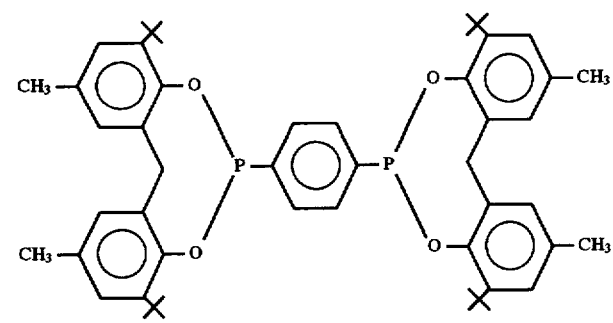
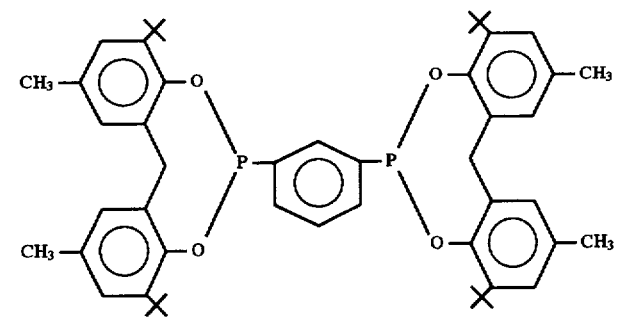

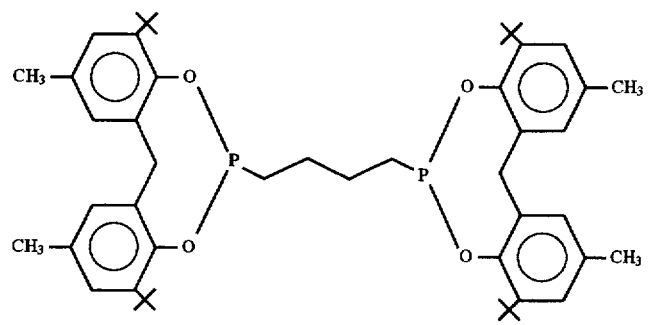
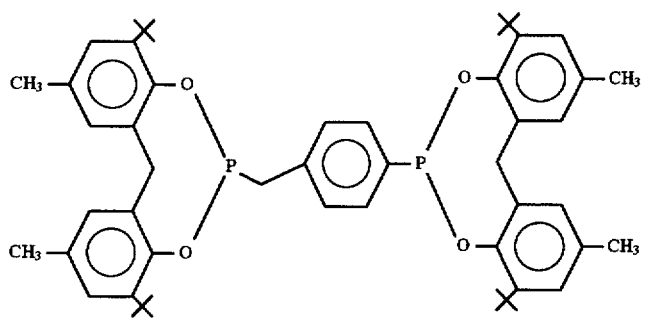
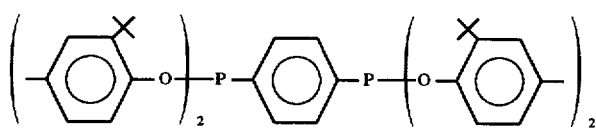
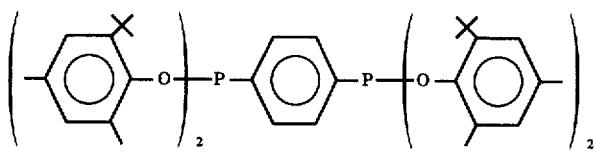
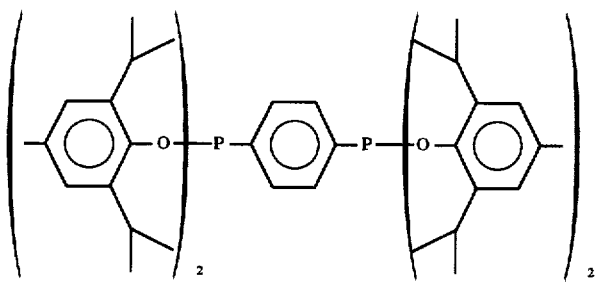
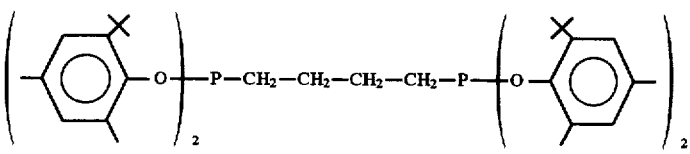
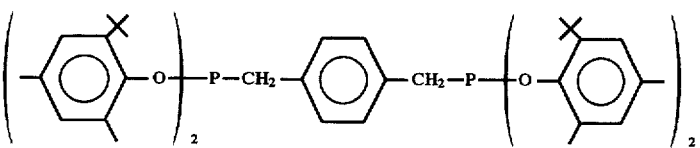

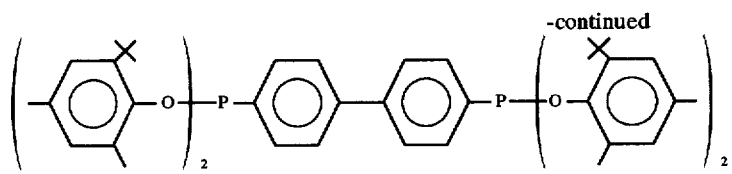

In the above structural formulas, + represents a t-butyl group, and >— represents an i-propyl group.

In the phosphonite compound of the above formula (1), $A^1$ is preferably a $C_{6-30}$ aryl group which may be substituted by an alkyl group, an aryl group, an alkoxy group, a dialkylamino group or a group of the formula —$SO_3Na$, and Q is preferably —$CR^1R^2$, wherein each of $R^1$ and $R^2$ which are independent of each other is a hydrogen atom or a $C_{1-6}$ alkyl group. The arylene group for $A^2$, $A^3$, $A^{10}$ and $A^{11}$ is preferably a 1,2-arylene group which may be substituted, particularly preferably a 1,2-phenylene group which may have a substituent such as a $C_{1-20}$ alkyl group or a $C_{1-20}$ alkoxy group at the 6-position and a substituent such as a $C_{1-20}$ alkyl group at one or more positions among the 3-, 4- and 5-positions, provided that the 1-position of the 1,2-phenylene group is bonded to the oxygen atom which is bonded to the phosphorus atom.

On the other hand, in the phosphonite compounds of the above-mentioned formulas (2) and (4), each of $A^5$, $A^6$, $A^{15}$ and $A^{16}$ is preferably a phenyl group having a $C_{1-20}$ alkyl group at the o-position, which may have other substituents on the benzene ring. $A^4$ is preferably a $C_{6-30}$ aryl group which may be substituted by an alkyl group, an aryl group, an alkoxy group, a dialkylamino group or a group of the formula —$SO_3Na$.

As the phosphinite compound used as a cocatalyst, a phosphinite compound of the following formula (5) may be mentioned as a specific example:

(5)

wherein each of $A^{23}$, $A^{24}$ and $A^{25}$ which are independent of one another, is an aryl group which may be substituted.

Specific examples of such a compound include the following compounds:

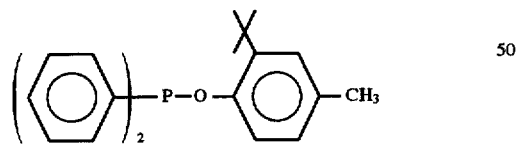

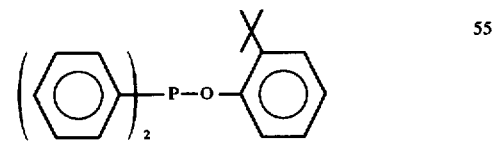

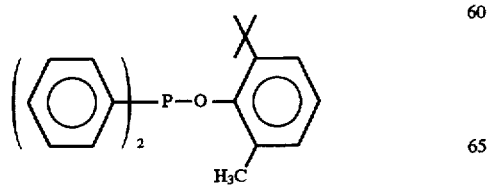

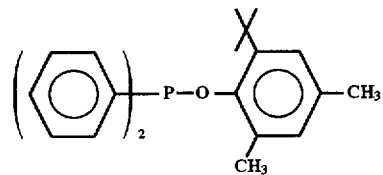

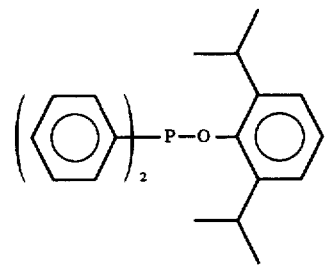

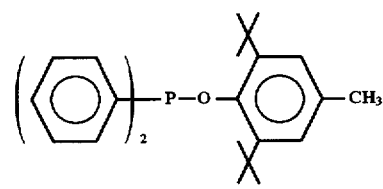

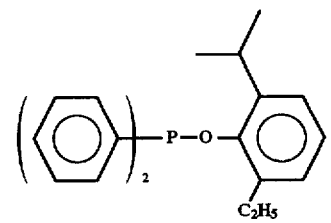

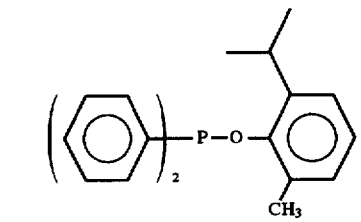

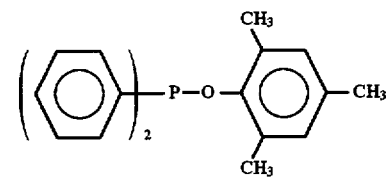

29
-continued
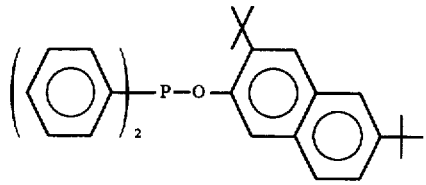
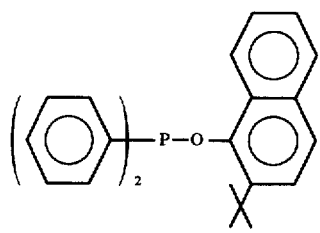
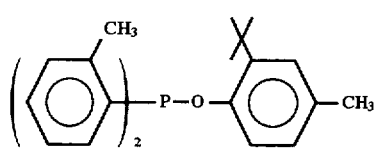
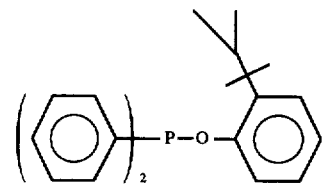
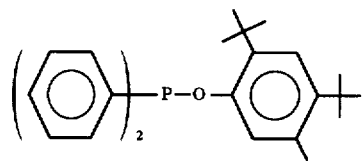
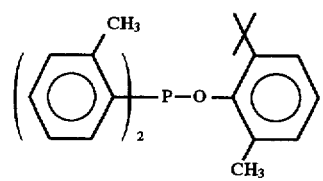
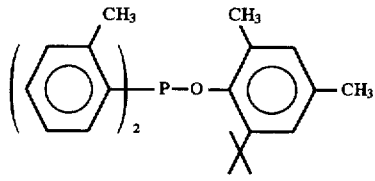
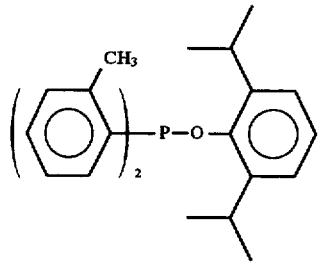
30
-continued
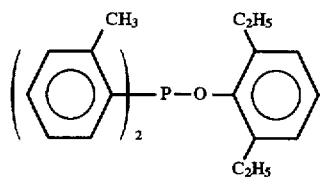
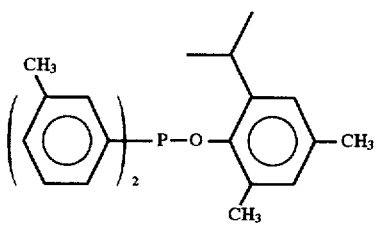
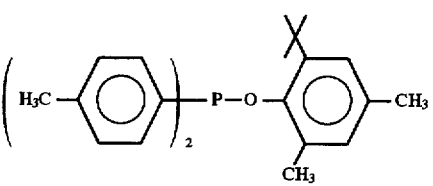
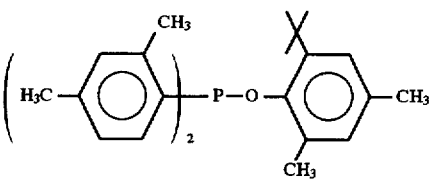
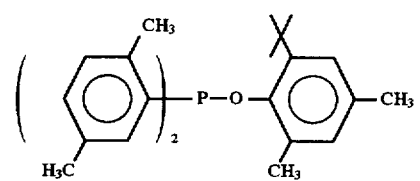
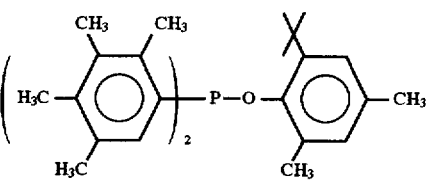
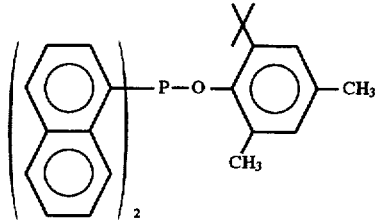

-continued

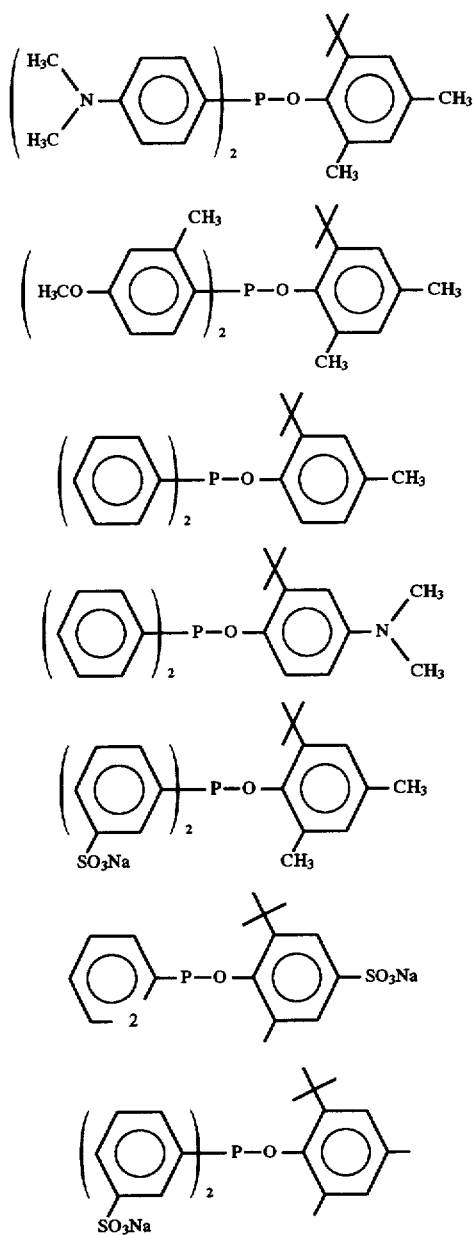

In the above structural formulas, + represents a t-butyl group, and ⊱ represents an i-propyl group.

In the phosphinite compound of the above formula (5), each of $A^{23}$ and $A^{24}$ is preferably a $C_{6-30}$ aryl group which may be substituted by an alkyl group, an aryl group, an alkoxy group, a dialkylamino group or a group of the formula —$SO_3Na$. $A^{25}$ is preferably an arylene group which may be substituted, particularly a phenyl group or a naphthyl group, which may have at least one substituent such as a $C_{1-20}$ alkyl group or a $C_{1-20}$ alkoxy group at the o-position, or a substituent such as a $C_{1-20}$ alkyl group, a $C_{1-20}$ alkoxy group or a group of the formula —$SO_3Na$ at the m-position and/or at the p-position.

As the phosphite compound to be used as a cocatalyst, a phosphite compound of the following formula (6) may be mentioned as a specific example.

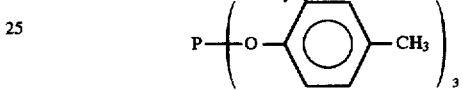

wherein each of $A^{25}$, $A^{27}$ and $A^{28}$ which are independent of one another, is an aryl group which may be substituted.

Specific examples of such a compound include the following compounds:

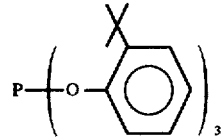

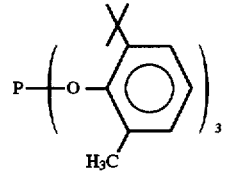

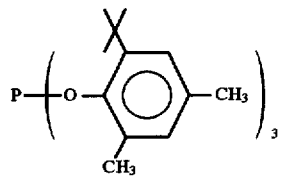

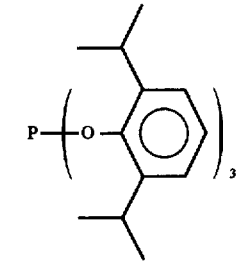

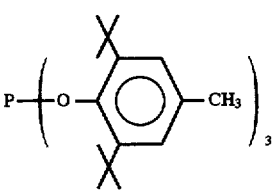

-continued

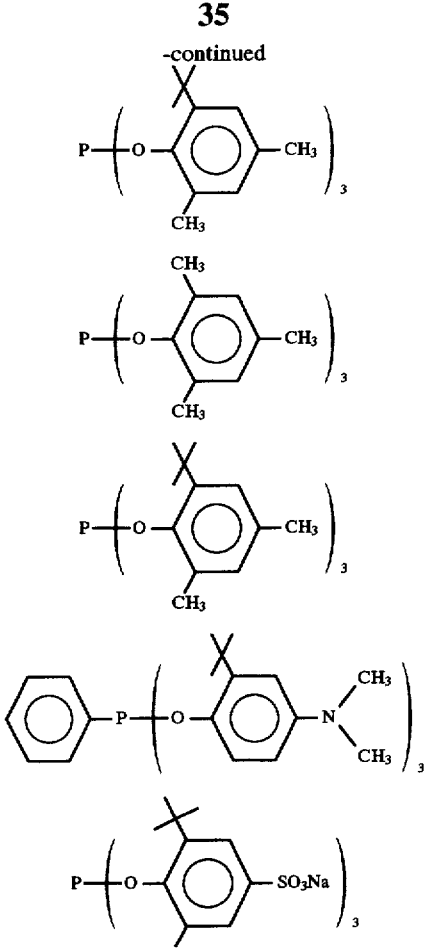

In the above structural formulas, + represents a t-butyl group, and >− represents an i-propyl group.

In the phosphite compound of the above formula (6), each of $A^{26}$, $A^{27}$ and $A^{28}$ which are independent of one another, is preferably an arylene group which may be substituted, particularly a phenyl group or a naphthyl group having at least one substituent such as a $C_{1-20}$ alkyl group or a $C_{1-20}$ alkoxy group at the o-position, or a substituent such as a $C_{1-20}$ alkyl group, a $C_{1-20}$ alkoxy group or a group of the formula —$SO_3Na$ at the m-position and/or the p-position.

Among phosphorus compounds having at least one trivalent phosphorus-oxygen single bond, those having both a phosphorus-oxygen single bond and a phosphorus-carbon single bond, such as a phosphonite compound and a phosphinite compound, are preferred.

Among phosphorus compounds having at least one trivalent phosphorus-oxygen single bond, it is a phosphonite compound which presents the optimum basicity of the ligand, and when a phosphonite compound is employed, it is possible to obtain the highest reaction rate and the highest selectivity for the desired compound.

The amount of the phosphorus compound having at least one trivalent phosphorus-oxygen single bond is usually selected within a range of from 0.1 to 250 mols, preferably from 2 to 150 mols, more preferably from 2 to 100 mols, (calculated as phosphorus atom) per gram atom of palladium.

In the present invention, the reaction of the conjugated alkadiene and water is carried out in the presence of the palladium compound, the phosphorus compound having at least one trivalent phosphorus-oxygen single bond and carbon dioxide. The carbon dioxide to be used in the present invention may be supplied in any form so long as it is present as carbon dioxide in the reaction system. For example, it may be in the form of molecular carbon dioxide, carbonic acid, a carbonate, a hydrogen carbonate or carbon dioxide, or an adduct of carbonic acid with an amine. The upper limit of the amount of carbon dioxide is determined from the economical reason, and even if it is used in an excess amount, there will be no particular adverse effect to the reaction. Carbon dioxide is used usually at least 1 mol, preferably at least 10 mols, per gram atom of palladium.

In the present invention, a basic compound may be present in the reaction solution for the purpose of stabilizing the palladium compound or the phosphorus compound in the reaction solution, or for the purpose of increasing the solubility of carbon dioxide to improve the reactivity or selectivity for the desired unsaturated alcohol compound. As such a basic compound, an amine compound, a pyridine derivative or an amide may, for example, be mentioned. Among them, an amine compound is particularly preferred. Such an amine compound is not particularly limited. However, a tertiary amine compound is most preferred, since a primary or secondary amine compound may sometimes gives a by-product by a side reaction with butadiene. Specific examples of such an amine compound include trialkylamines such as trimethylamine, triethylamine, tripropylamine, tributylamine and trioctylamine, amino alcohols such as 1-N,N-dimethylamino-2-propanol and 1-N,N-dimethylamino-3-butanol, heteroaromatic amines such as pyridine and 2,6-dimethylpyridine, alkoxyalkylamines such as N,N-dimethyl-2-methoxyethylamine and N,N-dimethyl-3-ethoxypropylamine, cyclic amines such as N-methylpyrrolidine, N-methylpiperidine, N-methylmorpholine and N,N'-dimethylpiperazine, and alkylenediamines such as N,N,N',N'-tetramethyl-1,3-butanediamine and N,N,N',N'-tetramethylhexamethylenediamine. Among these amines, triethylamine is particularly preferred taking into consideration various aspects such as the reaction results, the boiling point, the solubility, the price, etc.

The amount of such an amine compound is optionally selected usually within a range of from 0.01 to 20 parts by weight, preferably from 0.1 to 5 parts by weight, per part by weight of the alkadiene.

To conduct the above-mentioned reaction of the conjugated alkadiene and water, it is preferred to use a solvent to carry out the reaction smoothly. Useful solvents include ethers such as diethyl ether, dioxane, tetrahydrofuran, ethylene glycol dimethyl ether and tetraethylene glycol dimethyl ether, ketones such as acetone, methyl ethyl ketone, diethyl ketone, methyl isopropyl ketone and ethyl n-butyl ketone, nitriles such as acetonitrile, propionitrile and benzonitrile, aromatic hydrocarbons such as benzene, toluene, xylene and ethylbenzene, alkanes such as pentane, hexane and heptane alkenes such as hexene and octene, sulfoxides such as dimethylsulfoxide, sulfones such as sulforane, nitro compounds such as nitrobenzene and nitromethane, pyridine derivatives such as pyridine and α-picoline, amides such as acetamide, propionamide, N,N-dimethylformamide, N,N-dimethylacetamide and N,N-diethylacetamide, alcohols such as methanol, ethanol, n-propanol, isopropanol, n-butanol, isobutanol, t-butanol and n-alkanol, and carboxylic acids such as formic acid, acetic acid, propionic acid and butyric acid.

Such solvents may be used alone or in combination as a solvent mixture. Among them, when a lower alcohol is used, formation of a by-product such as an alkoxyalkadiene will be accompanied, and when a lower carboxylic acid is used, formation of a by-product such as an acylalkadiene will be accompanied, and therefore, a due care is required, as such formation of by-products makes the reaction system complicated.

The amount of the solvent is not particularly limited and is optionally selected usually within a range of from 0.1 to 50 parts by weight, preferably from 1 to 10 parts by weight, per part by weight of the conjugated alkadiene.

The reaction temperature for the reaction of the conjugated alkadiene and water may be selected within a range of from room temperature to 180° C. However, it is usual to select a temperature within a range of from 50° to 130° C., preferably from 75° to 110° C.

The reaction pressure is selected within a range of from atmospheric pressure to 200 kg/cm$^2$. In such a case, in addition to carbon dioxide, a gas inert to the reaction, such as nitrogen, helium or argon may be present.

In the present invention, the conjugated alkadiene and water are reacted under the above described reaction conditions to form an unsaturated alcohol having a structure formed by oligomerization of the conjugated alkadiene. The method of the present invention can be carried out by means of a well known technique such as a continuous system, a semicontinuous system or a batch system. The reaction product solution obtained by this reaction contains the catalyst, the unsaturated alcohol as the main product, by-products such as unsaturated hydrocarbons, unsaturated ethers, organic carboxylic acids and esters, as well as the solvent, an unreacted conjugated alkadiene and water. When the starting material conjugated alkadiene is 1,3-butadiene, the unsaturated alcohol having a structure obtained by even number oligomerization of 1,3-butadiene may be octa-2,7-dien-1-ol, octa-1,7-dien-3-ol, or 6-vinyl-2,8,13-tetradecatrien-1-ol, and by-products may, for example, be octatrienes, hexadecatetraenes, dioctadienyl ethers, organic carboxylic acids and esters.

According to the method of the present invention, the catalyst component functions effectively by using a palladium compound and a phosphorus compound having at least one trivalent phosphorus-oxygen single bond, as catalyst, whereby in the reaction of 1,3-butadiene and water, conventional unsaturated alcohols such as octa-2,7-dien-1-ol and octa-1,7-dien-3-ol can be obtained in good yield, and yet octa-2,7-dien-1-ol which is useful as a starting material for 1-octanol, can be obtained at high selectivity. Further, according to the method of the present invention, it is possible to obtain novel 6-vinyl-2,8-13-tetradecatrien-1-ol as a hydrated tetramer of 1,3-butadiene. Further, the unsaturated alcohol thereby obtained can be converted to the corresponding unsaturated alcohol by hydrogenation.

In the method for producing an unsaturated alcohol of the present invention, the reaction conditions may be suitably selected within the above-mentioned conditions depending upon the desired type of an unsaturated alcohol. However, to obtain octa-2,7-dien-1-ol in good yield at high selectivity, it is particularly preferred to conduct the reaction in the presence of a basic compound. On the other hand, to obtain 6-vinyl-2,8,13-tetradecatrien-1-ol in good yield, it is particularly preferred to conduct the reaction in the absence of a basic compound.

After the reaction, unsaturated alcohols may be separated by a suitable method such as a distillation method as disclosed in e.g., Japanese Unexamined Patent Publication No. 144306/1979 or an extraction method as disclosed in Japanese Unexamined Patent Publication No. 134427/1982. Further, to separate 6-vinyl-2,8,13-tetradecatrien-1-ol of the present invention from a hydration even number oligomerization reaction product of 1,3-butadiene, if a solvent having both hydrophilic and lipophilic natures, such as tetrahydrofuran, acetone or dimethylformamide, is used as the solvent for the above reaction, the reaction product solution may be distilled under reduced pressure to distill off the solvent, and then water-soluble compound serving as a ligand to palladium, such as sodium diphenylphosphinobenzene-m-sulfonate, water and hexane may be added thereto, followed by stirring, to separate the catalyst palladium in an aqueous phase and the product in a hexane phase, and then the hexane layer is distilled under reduced pressure to obtain the desired product. 6-Vinyl-2, 8,13-tetradecatrien-1-ol thus obtained, is useful as a starting material for various chemical industries, for example as a starting material for perfumes, cosmetics, plasticizers, adhesives, surfactants and intermediates for medicines. For example, a higher alcohol obtained by hydrogenating 6-vinyl-2,8,13-tetradecatrien-1-ol may be further esterified to be useful as a plasticizer or an adhesive, or may be converted to a sulfuric acid ester which is expected to be useful as a surfactant.

In the present invention, phosphonite compounds of the above formulas (7) and (8) are novel phosphonite compounds. With a compound of the formula (7) wherein the bisphenol moieties are non-symmetrical, a higher reaction rate is obtainable as compared with the one wherein the bisphenol moieties are symmetrical. Further, with a phosphonite compound of the formula (8), wherein the β-position is substituted by a branched alkyl group, a higher reaction rate and a higher selectivity for the desired compound can be obtained as compared with a phosphonite wherein the β-position is substituted by a non-branched alkyl group.

The phosphonite compounds can be produced by the following methods.

The asymmetrical bisphenol moieties of the phosphonite of the formula (7) can be prepared by adding to a phenol wherein at least one o-position is unsubstituted, an equivalent amount of an aldehyde compound by means of a base catalyst such as sodium hydroxide to prepare a phenol having methylol at the o-position and then reacting another molecule of a phenol wherein at least one o-position is unsubstituted, in the same manner.

The synthetic routes for phosphonites of the formulas (7) and (8) are common. However, there are two synthetic routes. Namely, the P—C bond may firstly be formed, and then the P—O bond may be formed. Otherwise, the order for the formation of the P—C bond and the P—O bond may be reversed. The P—C bond may be formed by preparing a Grignard reagent using an aryl bromide or an alkyl bromide as a starting material and then reacting the Grignard compound with phosphorus trichloride or bisphenoxyphosphine chloride. The P—O bond may be formed by reacting bisphenol with phosphorus trichloride or with an arylphosphine dichloride or an alkylphosphine dichloride by means of a basic compound such as a tertiary amine compound.

Further, in the present invention, a bis(phosphonite) palladium complex comprising a phosphonite compound of the above formula (1) or (2) and Pd is a novel palladium complex. It exhibits a high catalytic activity since it contains no extra ligand compound other than a phosphonite as a ligand. Further, depending upon the type of the reaction, there will be a merit that no introduction period will appear at the initial stage of the reaction. Further, if a palladium compound having a compound other than a phosphorus compound as a ligand is used in the reaction of the present application, a useless by-product will be formed by the reaction of the starting material alkadiene with the ligand, and the starting material alkadiene will be consumed uselessly. Whereas, by the use of a bis(phosphonite)palladium complex, such a disadvantage can be avoided.

Such a complex is formed during the process producing the catalyst for oligomerization of the conjugated alkadiene in the present invention. However, a common method for its preparation will be described as follows.

Using at least two equivalent of a phosphonite per equivalent of a palladium compound such as palladium acetate, telomerization of a conjugated alkadiene with an active hydrogen compound, such as butadiene with methanol, is conducted. After completion of the reaction, the precipitated crude palladium complex is collected by filtration and recrystallized from a solvent such as hexane to obtain the desired bis(phosphonite)palladium complex. Further, it is possible to prepare it by another method in which a bivalent compound of Pd is reacted with a reducing agent such as hydrazine in the presence of a phosphonite ligand in the same manner as a conventional method for preparing a zerovalent PdO phosphine complex.

Now, the present invention will be described in further detail with reference to Examples. However, it should be understood that the present invention is by no means restricted by such specific Examples.

EXAMPLE 1

Figure 2:
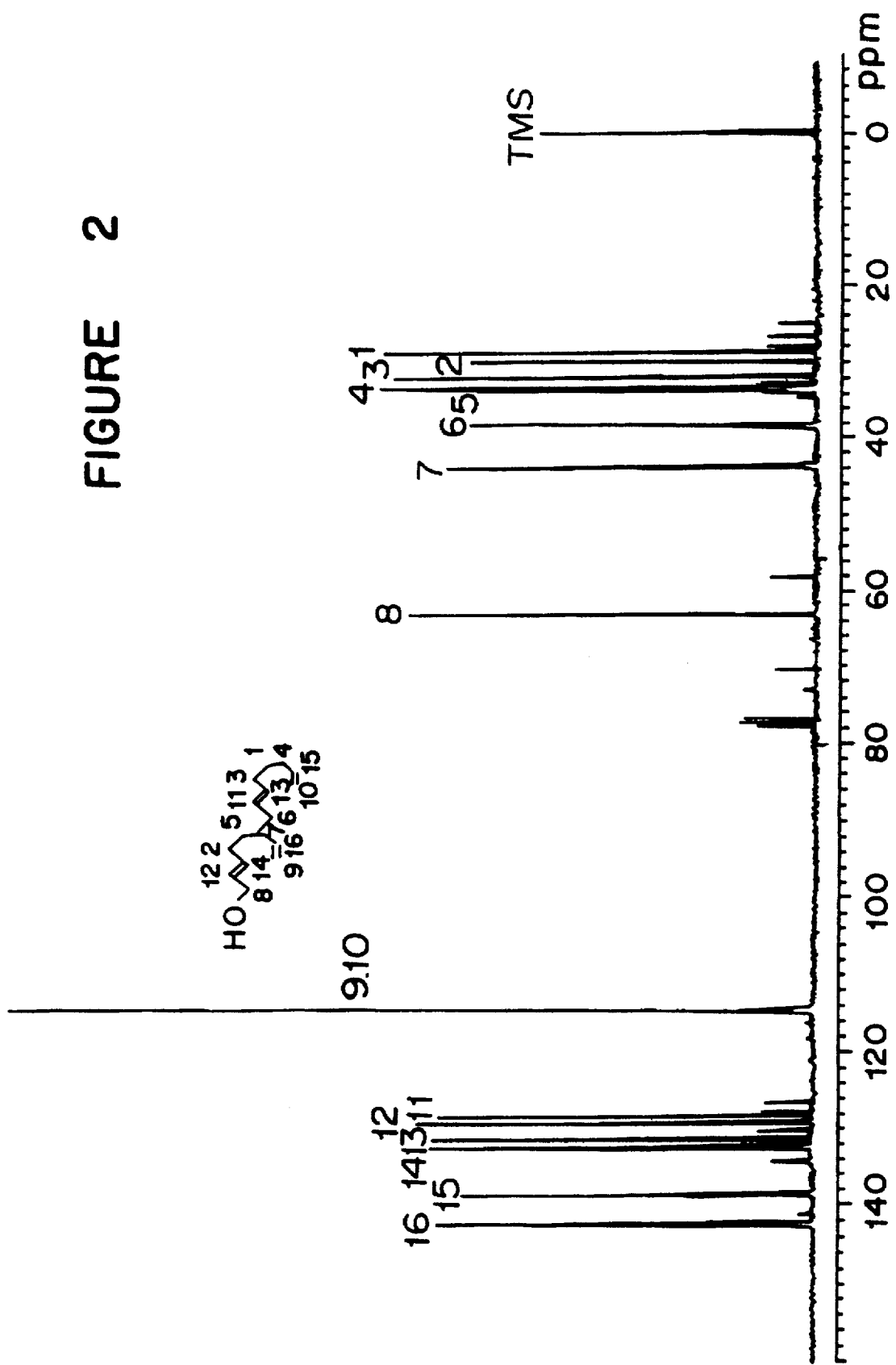
FIG. 2 shows a $^{13}$C-NMR spectrum of the high boiling point compound obtained in Example 1.
Figure 3:
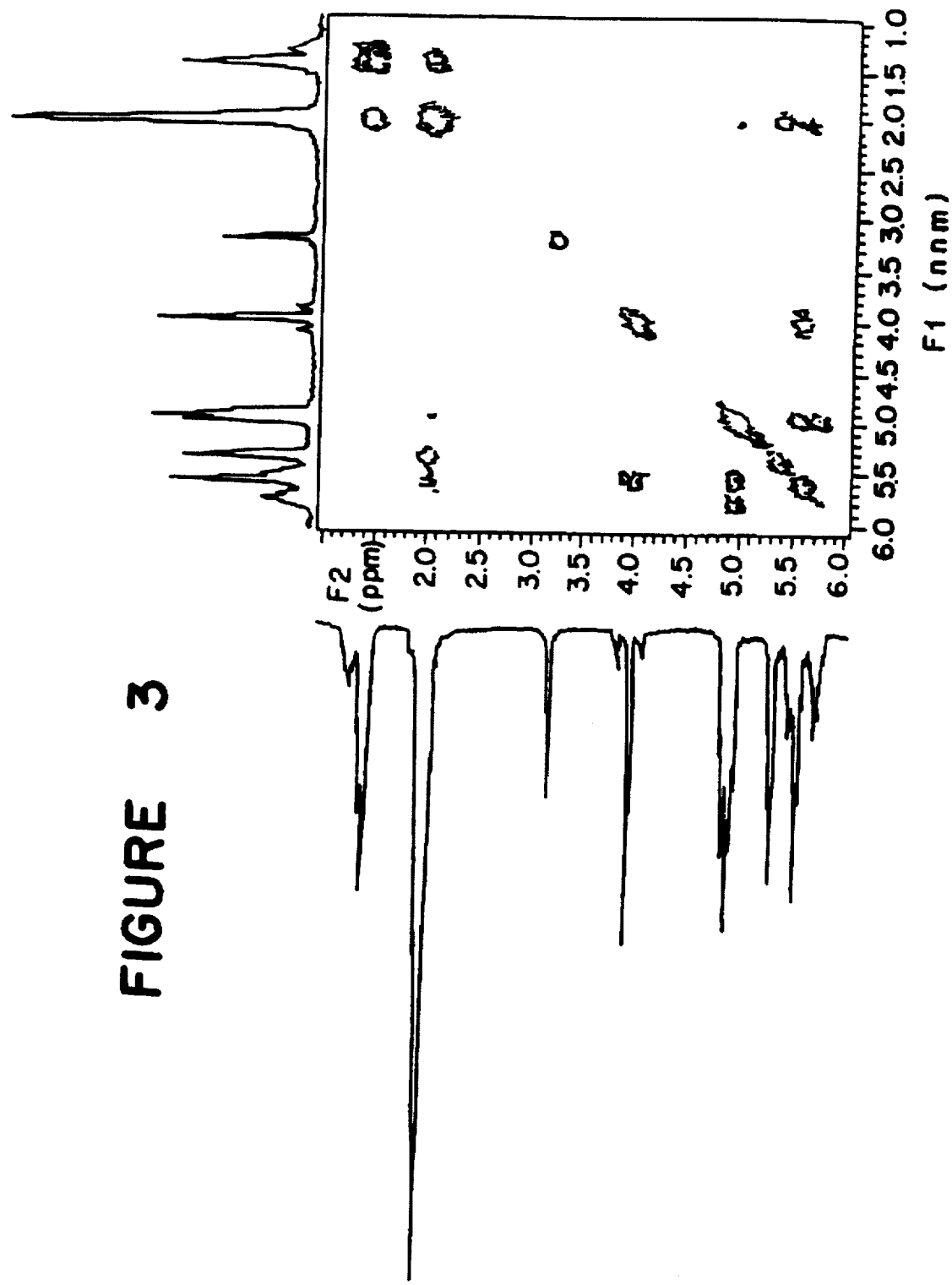
FIG. 3 shows a COSY spectrum of the high boiling point compound obtained in Example 1.
Figure 4:
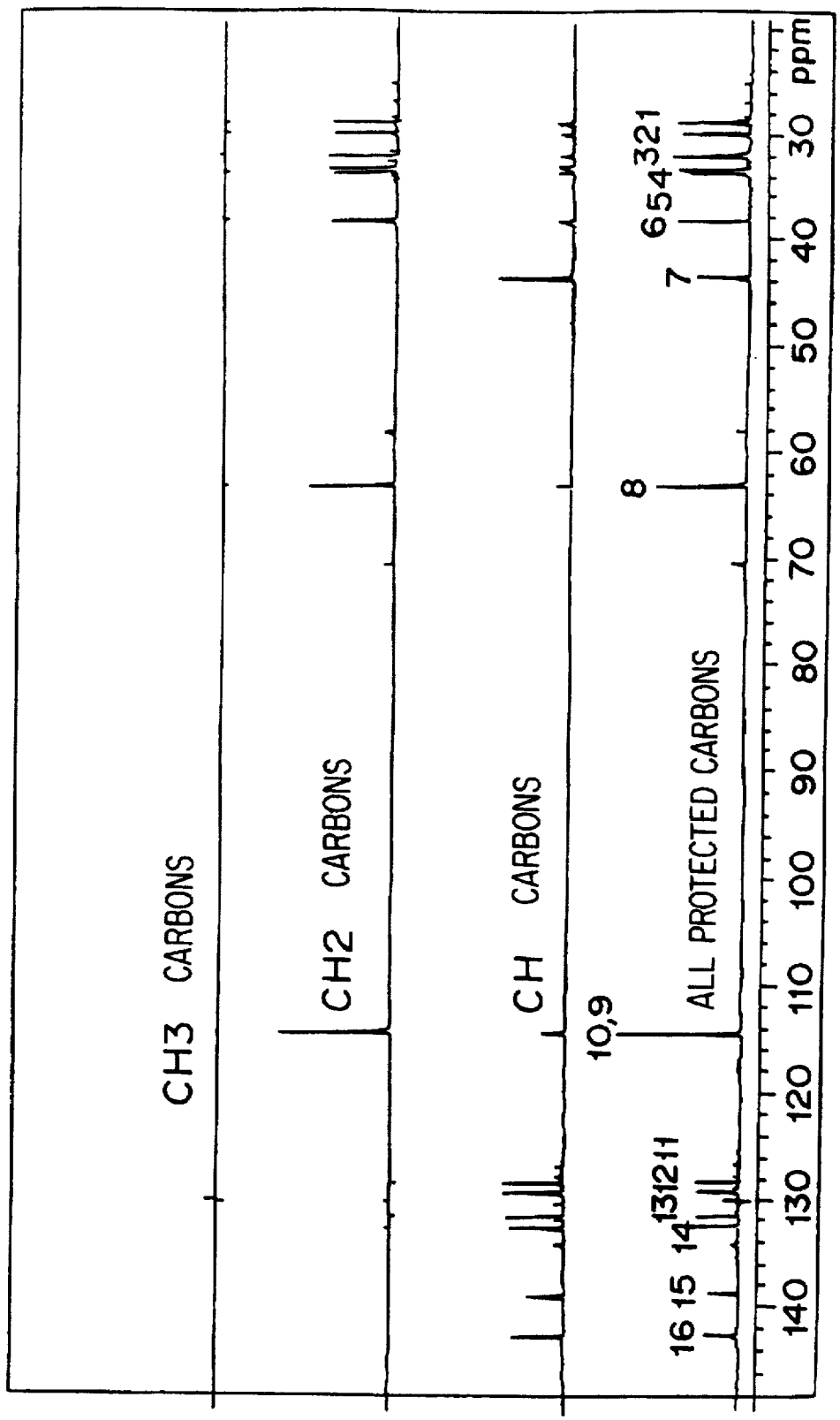
FIG. 4 shows a DEPT spectrum of the high boiling point compound obtained in Example 1.

Into a stainless steel autoclave having an internal capacity of 200 ml, 0.093 mmol palladium acetate, 0.38 mmol of phenyl(2,2'-methylenebis(6-t-butyl-4-methylphenoxy)) phosphine, 70 ml of acetone, 10 ml of water and 2.0 ml of o-xylene as an internal standard substance for a gas chromatography analysis, were charged under a nitrogen gas atmosphere. Further, 20.2 g of 1,3-butadiene and 8 g of carbon dioxide were introduced thereto. The reaction mixture was heated to bring the internal temperature to 90° C. over a period of 20 minutes with stirring at a rotational speed of 800 rpm. The reaction was continued at 90° C. for 3 hours, whereupon the reaction solution was analyzed by gas chromatography. As a result, as a yield based on the charged 1,3-butadiene, 51.7% of 2,7-ocatdien-1-ol (hereinafter referred to as 1HOD), 3.7% of 1,7-octdien-3-ol (hereinafter referred to as 3HOD) and 13.0% of a high boiling point compound (a non-identified compound having a higher boiling point than 1HOD and 3HOD) were obtained. Such a high boiling point compound was separated by the following method and identified. The above reaction solution was distilled under reduced pressure at 25° C. to distill off acetone. Then, 1 g of sodium diphenylphosphinobenzene-m-sulfonate, 20 ml of n-hexane and 20 ml of water were added thereto, and the mixture was stirred, followed by phase separation. The obtained hexane phase was distilled under reduced pressure, whereby 10.73 g in total of 1HOD and 3HOD were obtained under the conditions of about 2 mmHg at from 50° to 60° C. and 2.7 g of a later distilled component was obtained under the conditions of about 2 mmHg at from 115° to 145° C. The later distilled component was again purified by distillation under reduced pressure to obtain 0.93 g of an initial fraction under the conditions of about 2 mmHg at from 110° to 120° C. and 1.29 g of a later fraction. The purity of the later distilled component was 85% as measured by gas chromatography. Then, the NMR analysis of this later distilled component (solvent: $CDCl_3$) was carried out by means of UNITY 300, manufactured by Varian. FIG. 1 shows the $^1$H-NMR spectrum (300 MHz), FIG. 2 shows the $^{13}$C-NMR spectrum (75.429 MHz), FIG. 3 shows COSY (Correlation spectroscopy) spectrum (299.949 MHz), and FIG. 4 shows the DEPT (Distortionless Enhancement by polarization transfer) spectrum (75.43 MHz).

Figure 5:
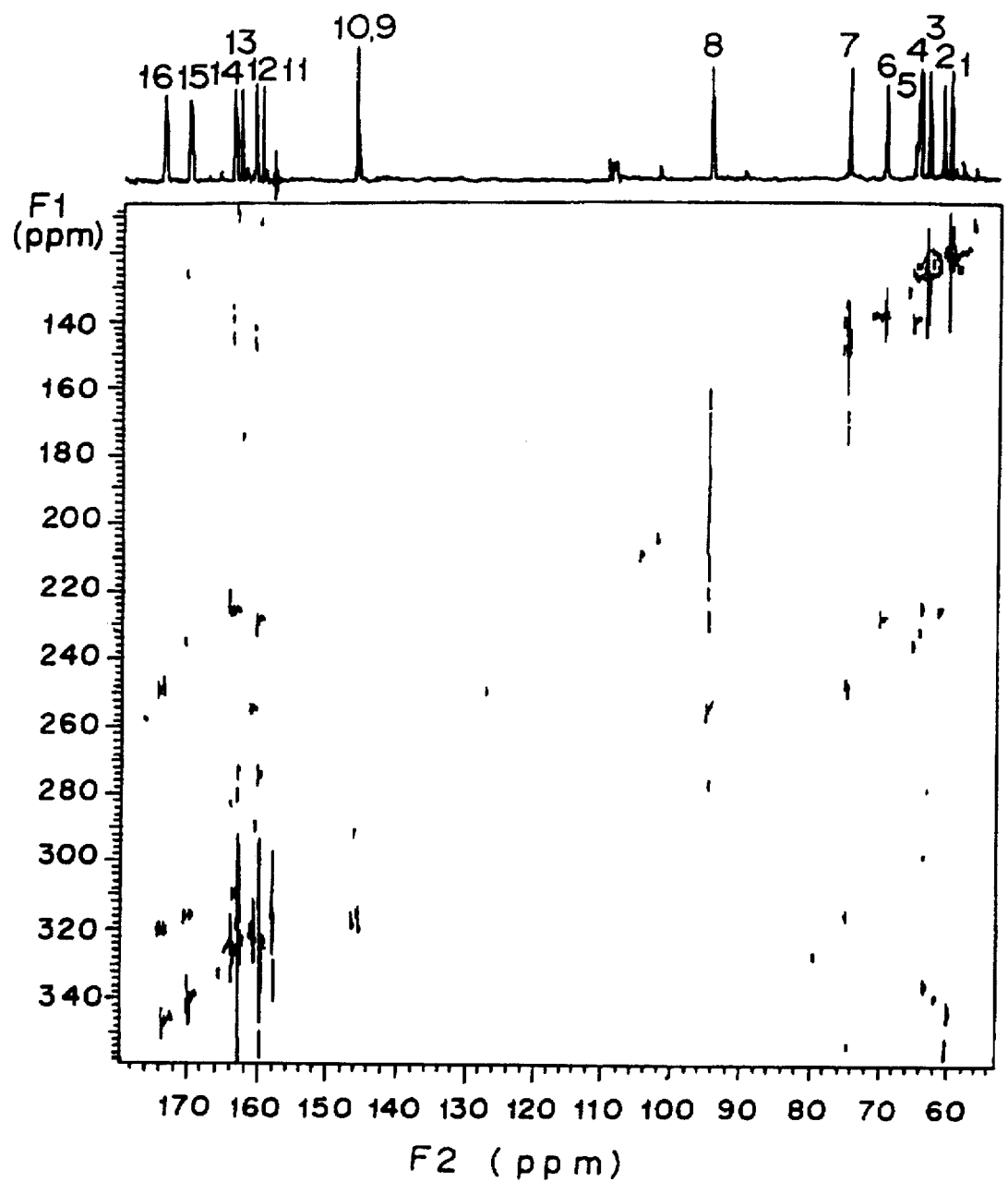
FIG. 5 shows the entire INADEQUATE spectrum at jcc 60.0 Hz of the high boiling point compound obtained in Example 1.
Figure 6:
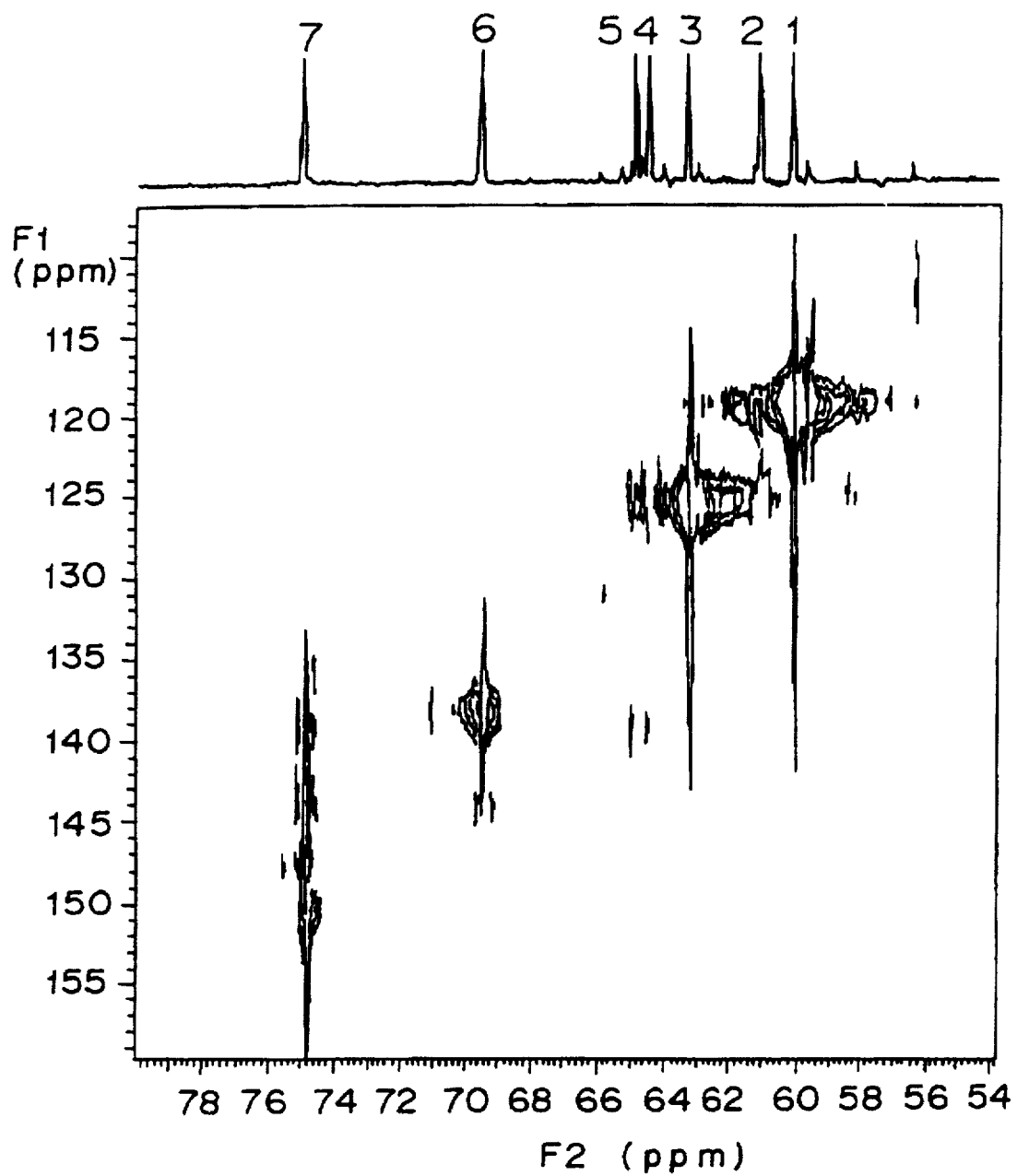
FIG. 6 shows an enlarged view of from 56 to 80 ppm of the spectrum shown in FIG. 5.
Figure 7:
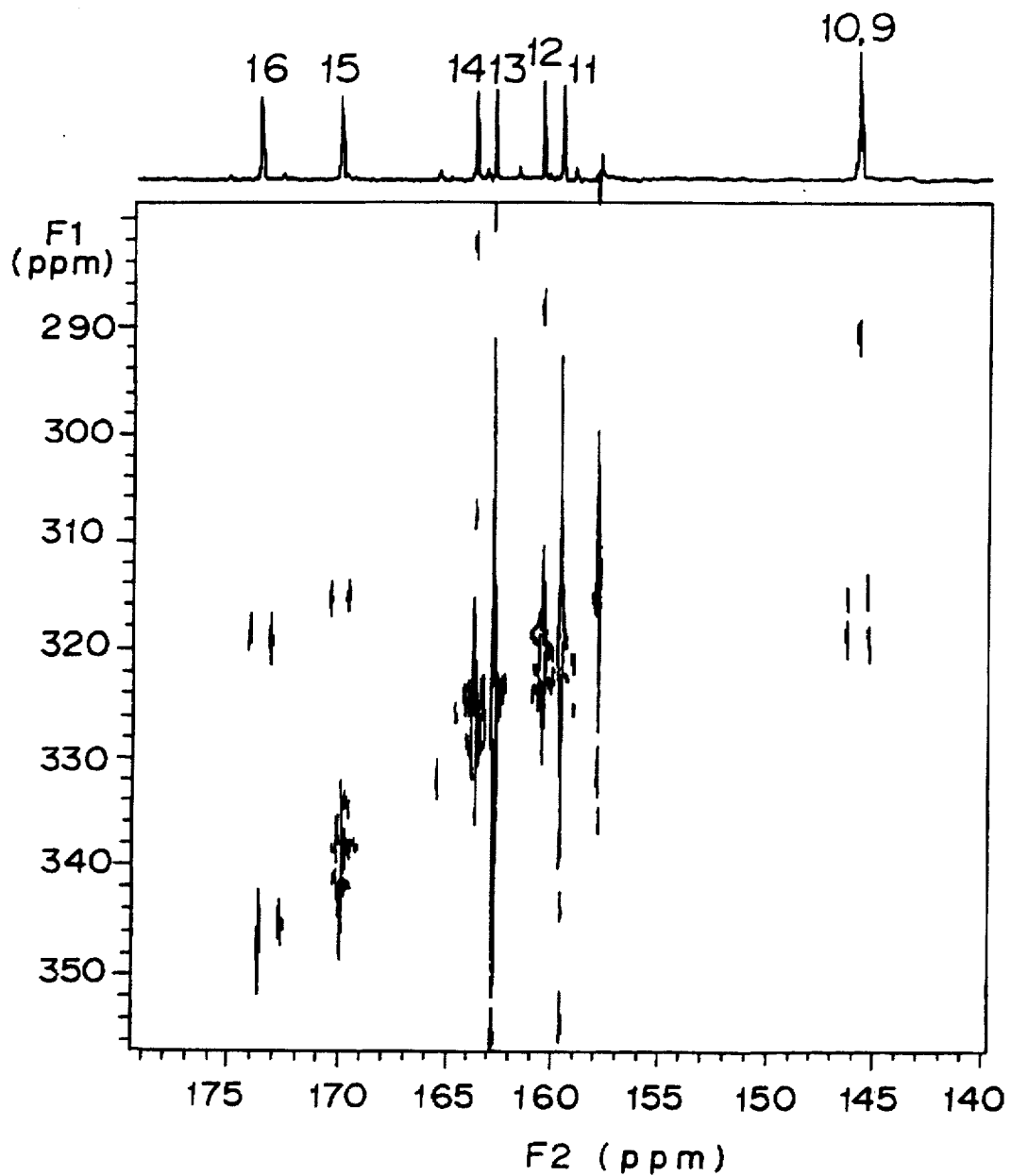
FIG. 7 shows an enlarged view of from 140 to 180 ppm of the spectrum shown in FIG. 5.
Figure 8:
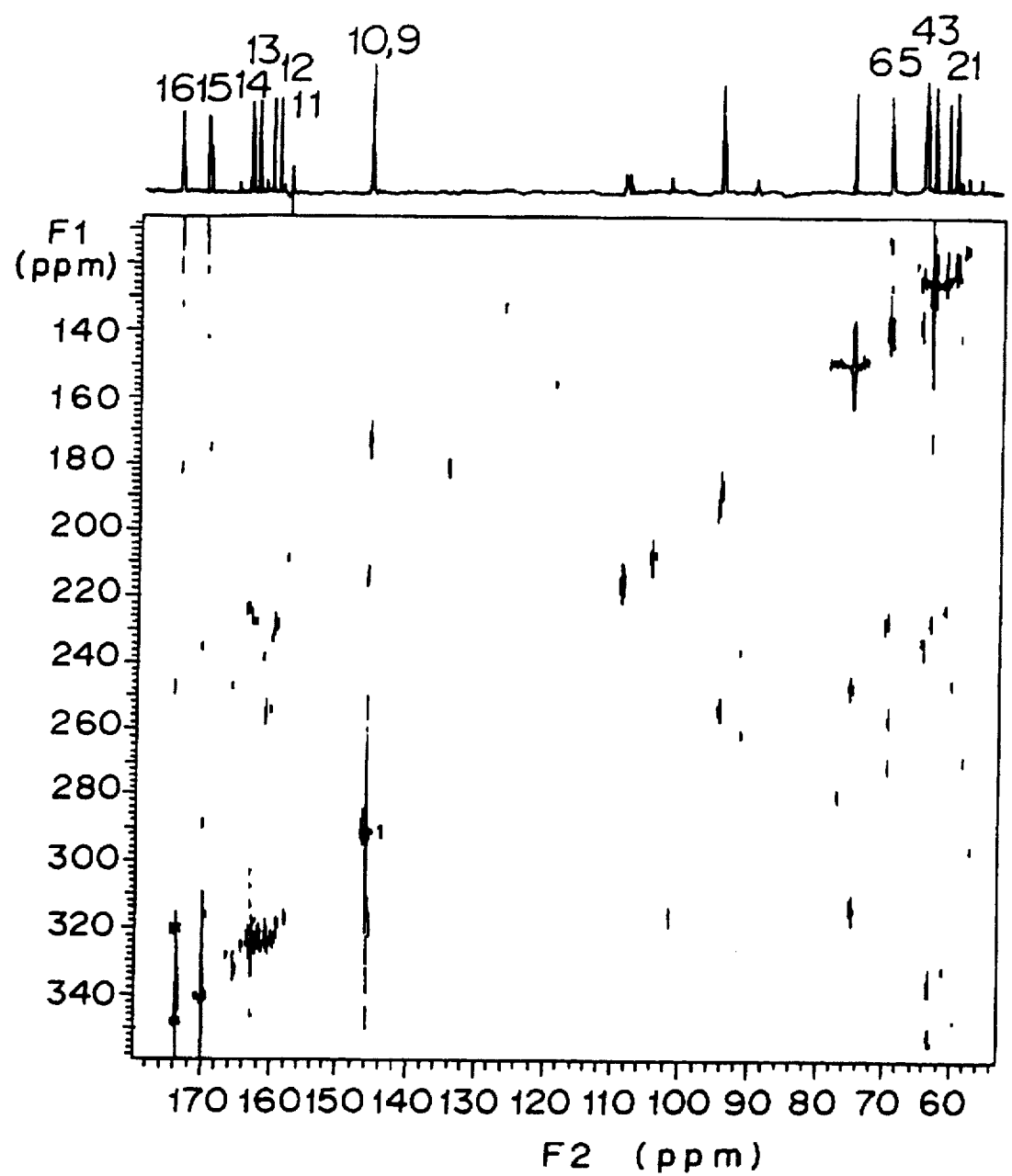
FIG. 8 shows the entire INADEQUATE spectrum at jcc 80.0 Hz of the high boiling point compound obtained in Example 1.
Figure 9:
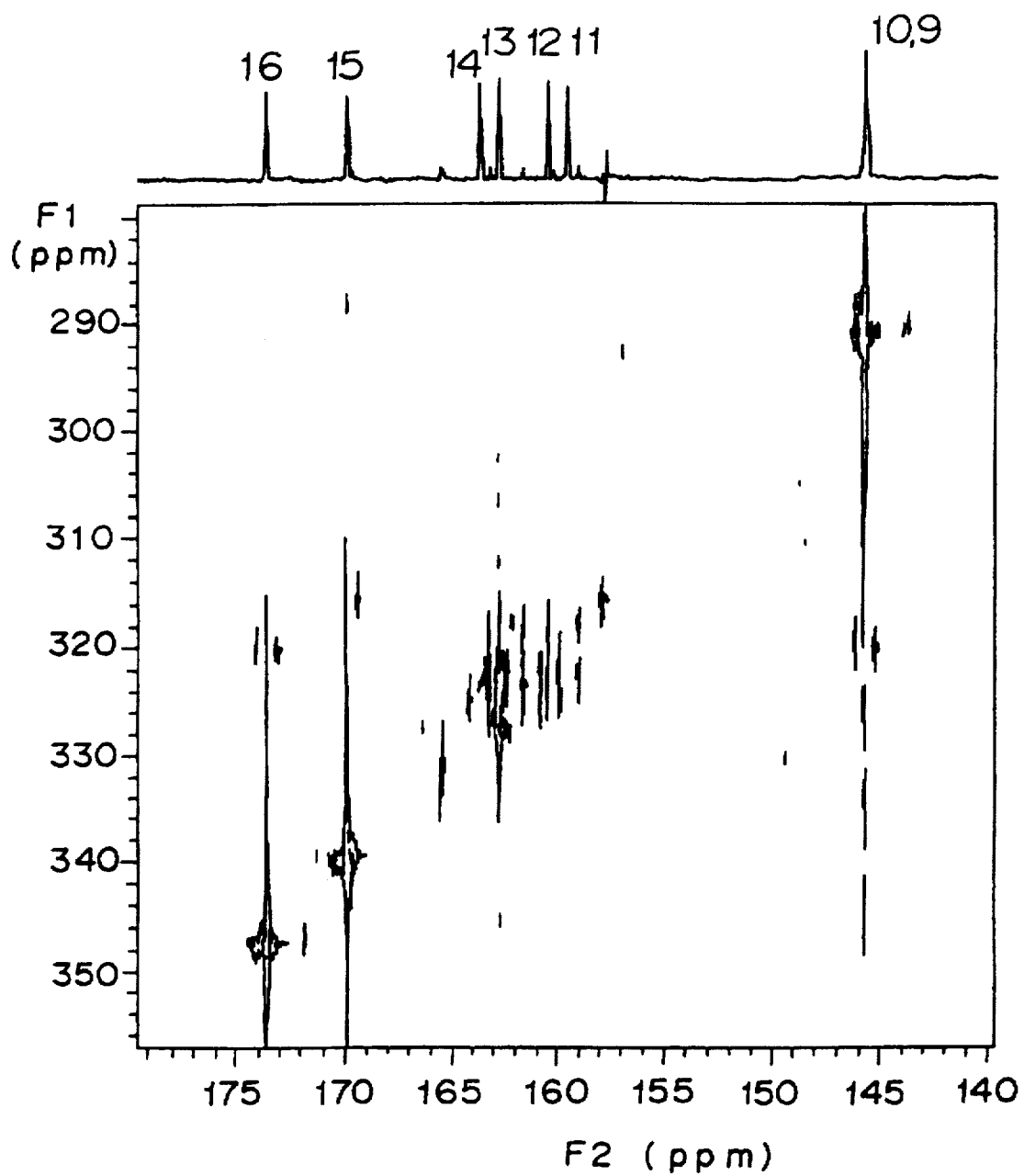
FIG. 9 shows an enlarged view of from 140 to 180 ppm of the spectrum shown in FIG. 8.

Further, FIGS. 5 to 9 show INADEQUATE (Incredible Natural Abundance Double E Quantum Transfer Experiment) spectra (75.929 MHz), wherein FIG. 5 is the entire spectrum at jcc 60.0 Hz, FIG. 6 is an enlarged view from 56 to 80 ppm in FIG. 5, FIG. 7 is an enlarged view from 140 to 180 ppm in FIG. 5, FIG. 8 is the entire spectrum at jcc 80.0 Hz, and FIG. 9 is an enlarged view from 140 to 180 ppm in FIG. 8. As a result of analyses of these spectra, the above high boiling point compound was confirmed to be 6-vinyl-2,8,13-tetradecatrien-1-ol (hereinafter referred to as 1HHDT) which is a tetramer hydrate of 1,3-butadiene.

EXAMPLE 2

Into a stainless steel autoclave having an internal capacity of 200 ml, 0.061 mmol of palladium acetate, 0.20 mmol of phenyl (2,2'-methylenebis(6-t-butyl-4-methylphenoxy)) phosphine, 47 ml-of acetone, 6.7 ml of water and 1.5 ml of o-xylene as an internal standard substance for the gas chromatography analysis, were charged under a nitrogen gas atmosphere. Further, 13.9 g of 1,3-butadiene and 8 g of carbon dioxide were introduced thereto. The reaction mixture was heated to bring the internal temperature to 90° C. over a period of 20 minutes with stirring at a rotational speed of 800 rpm. The reaction was continued at 90° C. for 4 hours, whereupon the reaction solution was analyzed by gas chromatography. The results are shown in Table 1.

EXAMPLE 3

The reaction was carried out in the same manner as in Example 2, except that the amount of the phosphonite was changed to 2.0 mmol, and the reaction time was changed to 3 hours. The results are shown in Table 1.

EXAMPLE 2

The reaction was carried out in the same manner as in Example 2, except that the amount of palladium acetate was changed to 0.5 mmol, the amount of the phosphonite was changed to 2.0 mmol, and the reaction time was changed to 30 minutes. The results are shown in Table 1.

EXAMPLE 5

The reaction was carried out in the same manner as in Example 2, except that the amount of the phosphonite was changed to 0.26 mmol, 47 ml of dimethylformamide was used instead of acetone as the solvent, and the reaction time was changed to 2 hours. The results are shown in Table 1.

EXAMPLE 6

The reaction was carried out in the same manner as in Example 2, except that the phosphonite was changed to 0.25 mmol of phenyl (2,2'-methylenebis(6-t-butyl-4-ethylphenoxy))phosphine, 11 ml of triethylamine was used in addition to acetone as the solvent for reaction, and the reaction time was changed to 2 hours. The results are shown in Table 1.

EXAMPLE 7

The reaction was carried out in the same manner as in Example 2, wherein the phosphonite was changed to 0.25 mmol of phenyl (2,2'-methylenebis(6-t-butyl-4-t-butylphenoxy))phosphine, and 11 ml of triethylamine was used in addition to acetone as the solvent for reaction, and the reaction time was changed to 3 hours. The results are shown in Table 1.

EXAMPLE 8

The reaction was carried out in the same manner as in Example 2, except that the phosphonite was changed to 2.7 mmol of phenyl di(2,6-diisopropyl-phenoxy)phosphine. The results are shown in Table 1.

EXAMPLE 9

The reaction was carried out in the same manner as in Example 2, except that the phosphonite was changed to 2.0 mmol of phenyl di(2,4-dimethyl-6-t-butylphenoxy) phosphine. The results are shown in Table 1.

EXAMPLE 10

The reaction was carried out in the same manner as in Example 2, except that the phosphonite was changed to 1.6 mmol of o-tolyl di(2,4-dimethyl-6-t-butylphenoxy) phosphine. The results are shown in Table 1.

COMPARATIVE EXAMPLE 1

While Examples 1 to 12 represent the results of using phosphonites, this Comparative Example shows the results of using a phosphine instead of a phosphonite.

The reaction was carried out in the same manner as in Example 2 except that instead of the phosphonite, 2.0 mmol of triphenylphosphine was used. The results are shown in Table 1.

COMPARATIVE EXAMPLES 2 and 3

The reaction was carried out in the same manner as in Comparative Example 1, except that the reaction time was changed to 30 minutes (Comparative Example 2) or one hour (Comparative Example 3). The results are shown in Table 1.

TABLE 1

|  | HOD yield (%)*1 | 1-HOD selectivity (%)*2 | 1-HHDT yield (%) *3 |
|---|---|---|---|
| Example 2 | 66.7 | 93.6 | 13.6 |
| Example 3 | 44.7 | 93.0 | 11.3 |
| Example 4 | 42.9 | 93.2 | 7.8 |
| Example 5 | 52.1 | 92.5 | 7.8 |
| Example 6 | 64.2 | 92.9 | 0.2 |
| Example 7 | 79.6 | 92.1 | 0.1 |
| Example 8 | 35.1 | 92.2 | 2.4 |
| Example 9 | 62.0 | 89.3 | 6.8 |
| Example 10 | 32.1 | 92.8 | 2.5 |
| Comparative Example 1 | 27.5 | 73.9 | 0.0 |
| Comparative Example 2 | 3.6 | 39.9 | 0.0 |
| Comparative Example 3 | 7.4 | 50.9 | 0.0 |

*1Total yield (%) of 1HOD and 3HOD based on 1,3-butadiene charged.
*2Amount (%) of 1HOD to the total amount of 1HOD and 3HOD.
*3Yield (%) of 1HHDT based on 1,3-butadiene charged.

EXAMPLE 11

The reaction was carried out in the same manner as in Example 2, except that the amount of palladium acetate was changed to 0.128 mmol, the phosphonite was changed to 2.0 mmol of phenyl di(2,4-dimethyl-6-t-butylphenoxy) phosphine, 1 ml of triethylamine was used in addition to acetone as the solvent for reaction, and the reaction time was changed to 2 hours. The results are shown in Table 2.

EXAMPLE 12

The reaction was carried out in the same manner as in Example 2, except that the amount of palladium acetate was changed to 0.134 mmol, the phosphonite was changed to 2.0 mmol of m-tolyl(2,2'-methylenebis(6-t-butyl-4-methylphenoxy))phosphine, the reaction time was changed to 3 hours, and the reaction temperature was changed to 75° C. The results are shown in Table 2.

EXAMPLE 13

The reaction was carried out in the same manner as in Example 2, except that the amount of palladium acetate was changed to 0.124 mmol, the phosphonite was changed to 2.0 mmol of m-tolyl(2,2'-methylenebis(6-t-butyl-4-methylphenoxy))phosphine, 3 ml of triethylamine was used in addition to acetone as the solvent for reaction, the reaction time was changed to 3 hours, and the reaction temperature was changed to 75° C. The results are shown in Table 2.

EXAMPLE 14

The reaction was carried out in the same manner as in Example 2, except that the amount of palladium acetate was changed to 0.129 mmol, the phosphonite was changed to 2.0 mmol of p-tolyl(2,2'-methylenebis(6-t-butyl-4-methylphenoxy))phosphine, the reaction time was changed to 3 hours, and the reaction temperature was changed to 75° C. The results are shown in Table 2.

EXAMPLE 15

The reaction was carried out in the same manner as in Example 2, except that the amount of palladium acetate was changed to 0.129 mmol, the phosphonite was changed to 2.0 mmol of p-tolyl(2,2'-methylenebis(6-t-butyl-4-methylphenoxy))phosphine, 3 ml of triethylamine was used in addition to acetone as the solvent for reaction, the reaction time was changed to 3 hours, and the reaction temperature was changed to 75° C. The results are shown in Table 2.

EXAMPLE 16

Into a stainless steel autoclave having an internal capacity of 30 ml, 0.192 mmol of palladium acetate, 3.1 mmol of phenyl di(2,4-dimethyl-6-(1,1,2-trimethylpropyl)phenoxy) phosphine, 70 ml of acetone and 10 ml of water were charged under a nitrogen gas atmosphere. Further, 20.3 g of 1,3-butadiene and 8 g of carbon dioxide were introduced thereto. The reaction mixture was heated to bring the internal temperature to 75° C. over a period of 20 minutes with stirring at a rotational speed of 800 rpm. The reaction was continued at 75° C. for 4 hours, whereupon the reaction solution was analyzed by gas chromatography. The results are shown in Table 2.

EXAMPLE 17

The reaction was carried out in the same manner as in Example 16, except that 1.35 ml of triethylamine was used in addition to acetone as the solvent for reaction. The results are shown in Table 2.

EXAMPLE 18

The reaction was carried out in the same manner as in Example 16, except that the phosphonite was changed to 1.9 mmol of phenyl(2,2'-methylenebis(6-(1,1,2-trimethylpropyl)-4-methylphenoxy))phosphine, and 0.67 ml of triethylamine was used in addition to acetone as the solvent for reaction. The results are shown in Table 2.

EXAMPLE 19

The reaction was carried out in the same manner as in Example 16, except that the phosphonite was changed to 1.54 mmol of phenyl(2,2'-methylenebis(6-t-butyl-4-t-octylphenoxy))phosphine as identified in the following formula. The results are shown in Table 2.

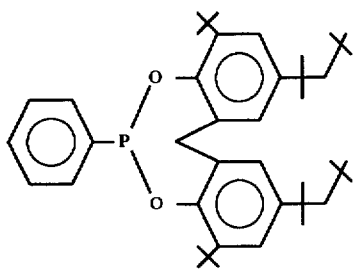

EXAMPLE 20

The reaction was carried out in the same manner as in Example 16, except that the phosphonite was changed to 1.55 mmol of phenyl(2,2'-methylenebis(6-t-butyl-4-t-octylphenoxy))phosphine, and 0.67 ml of triethylamine was used in addition to acetone as the solvent for reaction. The results are shown in Table 2.

EXAMPLE 21

The reaction was carried out in the same manner as in Example 16, except that the phosphonite was changed to 1.54 mmol of phenyl(2,2'-methylenebis(6-t-butyl-4-methoxyphenoxy))phosphine as identified in the following formula. The results are shown in Table 2.

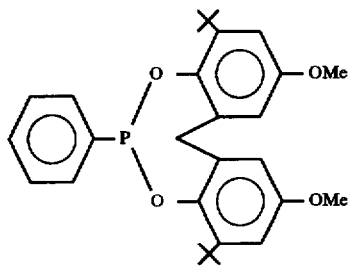

EXAMPLE 22

The reaction was carried out in the same manner as in Example 16, except that the phosphonite was changed to 1.54 mmol of phenyl(2,2'-methylenebis(6-t-butyl-4-methoxyphenoxy))phosphine, 1.35 ml of triethylamine was used in addition to acetone as the solvent for reaction, and the reaction time was changed to 3 hours. The results are shown in Table 2.

EXAMPLE 23

The reaction was carried out in the same manner as in Example 16, except that the phosphonite was changed to 1.54 mmol of phenyl(2,2'-ethylidenebis(4,6-di-t-butylphenoxy))phosphine as identified in the following formula. The results are shown in Table 2.

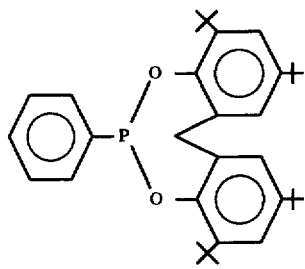

EXAMPLE 24

The reaction was carried out in the same manner as in Example 16, except that the phosphonite was changed to 1.54 mmol of phenyl(2,2'-ethylidenebis(4,6-di-t-butylphenoxy))phosphine as identified by the following formula, and 1.35 ml of triethylamine was used in addition to acetone as the solvent for reaction. The results are shown in Table 2.

EXAMPLE 25

The reaction was carried out in the same manner as in Example 16, except that the phosphonite was changed to 1.54 mmol of phenyl(2,2'-methylenebis(3-methyl-4,6-di-t-butylphenoxy))phosphine, and 1.35 ml of triethylamine was used in addition to acetone as the solvent for reaction. The results are shown in Table 2.

EXAMPLE 26

The reaction was carried out in the same manner as in Example 16, except that the phosphonite was changed to 1.54 mmol of phenyl(2,2'-methylenebis(6-isopropylphenoxy))phosphine, 2.65 ml of triethylamine was used in addition to acetone as the solvent for reaction, and the reaction time was changed to 5 hours. The results are shown in Table 2.

EXAMPLE 27

The reaction was carried out in the same manner as in Example 16, except that the phosphonite was changed to 1.55 mmol of phenyl(2,2'-methylenebis(6-phenylphenoxy))phosphine, 2.65 ml of triethylamine was used in addition to acetone as the solvent for reaction, and the reaction time was changed to 3 hours. The results are shown in Table 2.

EXAMPLE 28-1

The reaction was carried out in the same manner as in Example 16, except that the phosphonite was changed to 0.78 mmol of 4,4'-bis((2,2'-methylenebis(4-methyl-6-t-butylphenoxy))phosphino)biphenyl as identified by the following formula, 1.35 ml of triethylamine was used in addition to acetone as the solvent for reaction, and the reaction time was changed to 5 hours. The results are shown in Table 2.

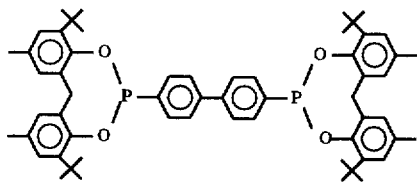

EXAMPLE 28-2

The reaction was carried out in the same manner as in Example 16, except that the phosphonite was changed to 0.78 mol of 4,4'-bis(bis(2,4-dimethyl-6-t-butylphenoxy) phosphino)bisphenyl as identified by the following formula, and the reaction temperature was changed to 90° C. The results are shown in Table 2.

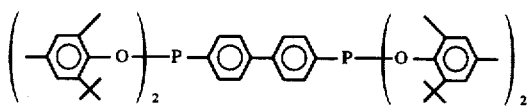

EXAMPLE 29

The reaction was carried out in the same manner as in Example 16, except that the phosphonite was changed to 1.56 mol of phenyl(5,3',5'-trimethyl-3-t-butyldiphenylmethane-2,2'-dioxy)phosphine as represented by the following formula, and 2.65 ml of triethylamine was used in addition to acetone as the solvent for reaction. The results are shown in Table 2.

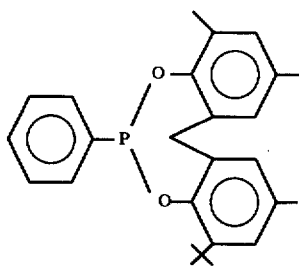

EXAMPLE 30

The reaction was carried out in the same manner as in Example 2, except that the amount of palladium acetate was changed to 0.123 mmol, the phosphonite was changed to 1.0 mmol of phenyl(5,3',5'-trimethyl-3-t-butyldiphenylmethane-2,2'-dioxy)phosphine as represented by the following formula, and 1.8 ml of triethylamine was used in addition to acetone as the solvent for reaction, and the reaction time was changed to 2 hours. The results are shown in Table 2.

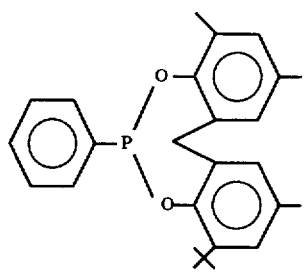

EXAMPLE 30

The reaction was carried out in the same manner as in Example 2, except that the amount of palladium acetate was changed to 0.128 mmol, and the amount of the phosphonite was changed to 2.00 mmol, 3 ml of triethylamine was used in addition to acetone as the solvent for reaction, the reaction temperature was changed to 60° C., and the reaction time was changed to 5 hours. The results are shown in Table 2.

TABLE 2

| Examples | HOD yield (%)*1 | 1-HOD selectivity (%)*2 | 1-HHDT yield (%) *3 |
|---|---|---|---|
| 11 | 69.3 | 81.2 | 0.9 |
| 12 | 43.3 | 62.6 | 12.5 |
| 13 | 83.7 | 85.5 | 0.4 |
| 14 | 49.9 | 69.8 | 10.2 |
| 15 | 57.7 | 84.5 | 0.3 |
| 16 | 58.8 | 71.0 | 8.0 |
| 17 | 71.9 | 81.4 | 1.0 |
| 18 | 73.7 | 81.3 | 3.1 |
| 19 | 65.7 | 74.3 | 7.6 |
| 20 | 75.5 | 85.9 | 0.8 |
| 21 | 52.9 | 68.3 | 8.0 |
| 22 | 77.4 | 87.0 | 1.0 |
| 23 | 66.7 | 77.0 | 6.2 |
| 24 | 73.9 | 81.3 | 0.8 |
| 25 | 42.6 | 63.9 | 0.1 |
| 26 | 55.6 | 73.7 | 0.5 |
| 27 | 28.7 | 58.9 | 2.6 |
| 28-1 | 81.0 | 83.7 | 1.2 |
| 28-2 | 60.0 | 89.2 | 6.9 |
| 29 | 73.8 | 80.0 | 2.2 |
| 30 | 76.1 | 80.8 | 1.4 |
| 31 | 69.7 | 92.0 | 0.2 |

*1Total yield (%) of 1HOD and 3HOD based on 1,3-butadiene charged.
*2Amount (%) of 1HOD to the total amount of 1HOD and 3HOD.
*3Yield (%) of 1HHDT based on 1,3-butadiene charged.

EXAMPLE 32

The reaction was carried out in the same manner as in Example 16, except that the phosphonite was changed to 3.07 mmol of phenyl(2,2'-methylenebis(4-methyl-6-di-t-butylphenoxy))phosphine, and 5 ml of N,N-dimethylpiperazine was used in addition to acetone as the solvent for reaction. The results are shown in Table 3.

EXAMPLE 33

The reaction was carried out in the same manner as in Example 16, except that the phosphonite was changed to 3.08 mmol of phenyl(2,2'-methylenebis(4-methyl-6-di-t-butylphenoxy))phosphine, and 5.8 ml of 2,6-lutidine was used in addition to acetone as the solvent for reaction. The results are shown in Table 3.

EXAMPLE 34

The reaction was carried out in the same manner as in Example 16, except that the phosphonite was changed to 3.07 mmol of phenyl(2,2'-methylenebis(4-methyl-6-di-t-butylphenoxy))phosphine, and 8.3 ml of N-methylmorpholine was used in addition to acetone as the solvent for reaction. The results are shown in Table 3.

EXAMPLE 35

The reaction was carried out in the same manner as in Example 16, except that the phosphonite was changed to 3.08 mmol of phenyl(2,2'-methylenebis(4-methyl-6-di-t-butylphenoxy))phosphine, 10.3 ml of N-ethylpyperidine was used in addition to acetone as the solvent for reaction, and the reaction time was changed to 2 hours. The results are shown in Table 3.

EXAMPLE 36

The reaction was carried out in the same manner as in Example 16, except that the phosphonite was changed to 3.07 mmol of phenyl(2,2'-methylenebis(4-methyl-6-di-t-butylphenoxy))phosphine, 0.8 ml of N,N-tetramethylhexanediamine was used in addition to acetone as the solvent for reaction, and the reaction time was changed to 2 hours. The results are shown in Table 3.

EXAMPLE 37

The reaction was carried out in the same manner as in Example 2, except that the amount of palladium acetate was changed to 0.139 mmol, the phosphonite was changed to 2.0 mmol of phenyl(2,2'-methylenebis(4,6-di-t-butylphenoxy)) phosphine, 3 ml of pyridine was used in addition to acetone as the solvent for reaction, and the reaction temperature was changed to 75° C. The results are shown in Table 3.

EXAMPLE 38

The reaction was carried out in the same manner as in Example 2, except that the amount of palladium acetate was changed to 0.123 mmol, the phosphonite was changed to n-butyl(2,2'-methylene-4-methyl-6-t-butylphenyl) phosphine, 3 ml of triethylamine was used in addition to acetone as the solvent for reaction, and the reaction time was changed to 0.5 hour. The results are shown in Table 3.

EXAMPLE 39

The reaction was carried out in the same manner as in Example 16, except that the phosphonite was changed to 3.08 mmol of phenyl(2,2'-methylenebis(4-methyl-6-di-t-butylphenoxy))phosphine, 0.03 ml of N-methylimidazole was used in addition to acetone as the solvent for reaction. The results are shown in Table 3.

EXAMPLE 40

The reaction was carried out in the same manner as in Example 16, except that the phosphonite was changed to 3.08 mmol of phenyl(2,2'-methylenebis(4-methyl-6-di-t-butylphenoxy))phosphine, 0.2 mmol of 1,10-phenanthroline was used in addition to acetone as the solvent for reaction, and the reaction was conducted for 6 hours. The results are shown in Table 3.

EXAMPLE 41

The reaction was carried out in the same manner as in Example 16, except that the phosphonite was changed to 3.08 mmol of phenyl(2,2'-methylenebis(4-methyl-6-di-t-butylphenoxy))phosphine, and 0.19 mmol of 2,2'-bipyridine was used in addition to acetone as the solvent for reaction. The results are shown in Table 3.

TABLE 3

| Examples | HOD yield (%)*1 | 1-HOD selectivity (%)*2 | 1-HHDT yield (%) *3 |
|---|---|---|---|
| 32 | 63.6 | 84.4 | 0.5 |
| 33 | 65.0 | 82.2 | 4.0 |
| 34 | 72.8 | 84.5 | 0.7 |
| 35 | 76.3 | Not measured | 0.3 |
| 36 | 52.0 | 71.4 | 0.1 |
| 37 | 72.6 | 76.8 | 1.1 |
| 38 | 9.6 | 88.3 | 0.1 |
| 39 | 59.0 | 81.9 | 3.1 |
| 40 | 28.6 | 82.9 | 1.1 |
| 41 | 51.4 | 74.1 | 5.5 |

*1Total yield (%) of 1HOD and 3HOD based on 1,3-butadiene charged.
*2Amount (%) of 1HOD to the total amount of 1HOD and 3HOD.
*3Yield (%) of 1HHDT based on 1,3-butadiene charged.

EXAMPLE 42

This Example shows that by an addition of an amine to the reaction system, the phosphonite compound can be stably maintained without decomposition even when the reaction product was recycled.

Into a stainless steel autoclave having an internal capacity of 200 ml, 0.127 mmol of palladium acetate, 2.03 mmol of phenyl(2,2'-methylenebis(4,6-di-t-butylphenoxy)) phosphine, 47 ml of acetone, 6.7 ml of water, 7 ml of triethylamine and 3 ml of trioctylamine were charged under a nitrogen gas atmosphere. Further, 13.8 g of 1,3-butadiene and 8 g of carbon dioxide were introduced thereto. The reaction mixture was heated to bring the internal temperature to 75° C. over a period of 20 minutes with stirring at a rotational speed of 800 rpm. The reaction was continued at 75° C. for 2 hours, whereupon the reaction solution was analyzed by gas chromatography, whereby 64.3% of 1HOD, 3.9% of 3HOD and 0.3% of 1HHDT were obtained as the yield per 1,3-butadiene charged. This reaction solution was distilled under reduced pressure at 25° C. to distill off acetone, triethylamine and water, and then distilled under a reduced pressure of about 2 mmHg at a bath temperature of 90° C. to distill off HOD to obtain 3.93 g of the distillation residue. The distillation residue was analyzed by $^{31}$P-NMR, whereby signals of a phosphonite and phosphonite oxide were detected at 164.3 ppm and 12.5 ppm, respectively, based on phosphoric acid. Into the above autoclave, the entire amount of this distillation residue, 47 ml of acetone, 6.7 ml of water and 7 ml of triethylamine were charged. Further, 13.5 g of 1,3-butadiene and 8 g of carbon dioxide were introduced, and the mixture was reacted in the same manner as the first time, whereupon the reaction solution of the second time was analyzed by gas chromatography, whereby 74.6% of 1HOD, 4.3% of 3HOD and 0.4% of 1HHDT were obtained, as the yield per 1,3-butadiene charged. The reaction solution of the second time was analyzed by $^{31}$P-NMR, whereby signals of a phosphonite and a phosphonite oxide were detected at 164.1 ppm and 12.4 ppm, respectively, based on phosphoric acid. This reaction solution was subjected to distillation under reduced pressure at 25° C. to distill off acetone, triethylamine and water and then distilled under a reduced pressure of about 2 mmHg at a bath temperature of 90° C. to distill off HOD and to obtain 4.09 g of a distillation residue. The distillation residue of the second time was analyzed by $^{31}$P-NMR, whereby signals of a phosphonite and a phosphonite oxide were detected at 164.3 ppm and 12.5 ppm, respectively, based on phosphoric acid. Into the above autoclave, the entire amount of this distillation residue of second time, 47 ml of acetone, 6.7 ml of water and 7 ml of triethylamine were charged. Further, 13.5 g of 1,3-butadiene and 8 g of carbon dioxide were introduced thereto. The mixture was reacted in the same manner as in the first and second times. The reaction solution of the third time was analyzed by gas chromatography, whereby 62.7% of 1HOD, 3.8% of 3HOD and 0.2% of 1HHDT were obtained as the yield per 1,3-butadiene charged. The reaction solution of the third time was analyzed by $^{31}$P-NMR, whereby signals of a phosphonite and a phosphonite oxide were detected at 164.1 ppm and 12.4 ppm, respectively, based on phosphoric acid. Thus, no decomposition of the phosphonite was observed by the repetition of the reaction for three times.

EXAMPLE 43

Into a stainless steel autoclave having an internal capacity of 200 ml, 0.065 mmol of palladium acetate, 0.51 mmol of phenyl(2,2'-methylenebis(4-methyl-6-t-butylphenoxy)) phosphine, 47 ml of acetone and 6.7 mmol of water were charged under a nitrogen gas atmosphere. Further, 13.5 g of 1,3-butadiene and 8 g of carbon dioxide were introduced thereto. The reaction mixture was heated to bring the internal temperature to 90° C. over a period of 20 minutes with stirring at a rotational speed of 800 rpm. The reaction was continued at 90° C. for 3 hours. Then, the reaction solution was analyzed by gas chromatography, whereby 47.5% of 1HOD, 3.6% of 3HOD and 8.9% of 1HHDT were obtained as the yield per 1,3-butadiene charged. This reaction solution was subjected to distillation under reduced pressure at 25° C. to distill off acetone and water and then distilled under a reduced pressure of about 2 mmHg at a bath temperature of 130° C. to distill off HOD and HHDT and to obtain 5.49 g of a distillation residue. Into the above autoclave, the entire amount of this distillation residue, 47 ml of acetone and 6.7 ml of water were charged. Further, 13.6 g of 1,3-butadiene and 8 g of carbon dioxide were introduced thereto, and the mixture was reacted in the same manner as in the first time. The reaction solution of the second time was analyzed by gas chromatography, whereby 39.0% of 1HOD, 2.6% of 3HOD and 6.4% of 1HHDT were obtained as the yield per 1,3-butadiene charged. This reaction solution was subjected to distillation under reduced pressure at 25° C. to distill off acetone and water and then distilled under a reduced pressure of about 2 mmHg at a bath temperature of 130° C. to distill off HOD and HHDT and to obtain 6.09 g of a distillation residue. To the above autoclave, the entire amount of this distillation residue of the second time, 47 ml of acetone and 6.7 ml of water were charged. Further, 13.8 g of 1,3-butadiene and 8 g of carbon dioxide were introduced thereto, and the mixture was reacted in the same manner as in the first and second times. The reaction solution of the third time was analyzed by gas chromatography, whereby 28.4% of 1HOD, 1.8% of 3HOD and 3.8% of 1HHDT were obtained as the yield per 1,3-butadiene charged. The reaction solution of the third time was analyzed by $^{31}$P-NMR, whereby a signal of a phosphonite oxide and a signal of a decomposition product of the phosphonite were detected at 12.4 ppm and 44.7 ppm, respectively, based on phosphoric acid, and no original phosphonite was detected.

EXAMPLE 44

Preparation of a palladium(phosphonite)$_2$ complex

Into a stainless steel microautoclave having an internal capacity of 70 ml, 1.01 mmol of palladium acetate, 5.01 mmol of phenyl(2,2'-methylenebis(4-methyl-6-t-butylphenoxy))phosphine, 10 ml of methanol and 2 ml of tritylamine were charged under a nitrogen gas atmosphere. Further, 3.3 g of 1,3-butadiene was introduced thereto. The reaction mixture was reacted in an electric furnace at 80° C. for 1.5 hours with stirring by a magnetic stirrer. The reaction solution was taken out, and the gray precipitate formed was collected by filtration. To the obtained gray precipitate, 15 ml of deaerated hexane was added under a nitrogen stream, and the mixture was stirred. An insoluble component was filtered off to obtain a yellow hexane solution, which was concentrated to about ⅓, whereby yellow crystals precipitated. The crystals were collected by filtration and dried to obtain a desired palladium(phosphonite)$_2$ complex. As a result of the elemental analysis, the atomic ratio of phosphorus/palladium was 1.99, and $^{31}$P-NMR and $^1$H-NMR were measured, respectively, in acetone d6 solvent, whereby data as shown in Table 4 were obtained, and the obtained yellow crystals were confirmed to be bis(2,10-dimethyl-4,8-bis(1,1-dimethylethyl)-6-phenyl-12H-dibenzo[d,g][1,3,2]dioxaphosphocin)palladium.

TABLE 4

|   | Yellow complex | Original phosphonite |
|---|---|---|
| P | 160.7 ppm | 164.2 ppm |
| H | 1.00 ppm (36H s) | 1.22 ppm (18H s) |
|   | 2.40 ppm (12H s) | 2.29 ppm (6H s) |
|   | 3.39 ppm (2H d J=12.9 Hz) | 3.51 ppm (1H d J=12.6 Hz) |
|   | 4.17 ppm (2H d J=12.8 H) | 4.46 ppm (1H dd J=12.6, 3.3 H) |
|   | 7.04 ppm (4H s) | 7.08 ppm (2H) |
|   | 7.21 ppm (4H s) | 7.32 ppm (2H) |
|   | 7.56 ppm (6H m) | 7.64 ppm (3H) |
|   | 7.83 ppm (4H m) | 8.03 ppm (2H) |

EXAMPLE 45-1

The reaction was carried out in the same manner as in Example 2, except that 1.1 mmol of the palladium complex prepared in Example 44 was used instead of palladium acetate, 3 ml of triethylamine was used in addition to acetone as the solvent for reaction, and the reaction temperature was changed to 75° C. As a result, the yield of HOD was 81.5%, the selectivity for 1HOD was 83.4%, and the yield of 1HHDT was 0.5%.

EXAMPLE 45-2

The experiment of Example 40 using the complex was carried out by changing the reaction time to 30 minutes or one hour. (3 ml of triethylamine was used in addition to acetone as the solvent for reaction, the reaction temperature was changed to 75° C., the reaction time was 30 minutes or one hour, and a small amount of the reaction solution was withdrawn from the reactor and analyzed.)

|  | HOD yield (%)*$^1$ | 1-HOD selectivity (%)*$^2$ | 1-HHDT yield (%) *$^3$ |
|---|---|---|---|
| 30 Minutes | 27.5 | 76.3 | 0.4 |
| 1 Hour | 52.5 | 78.9 | 0.4 |

*$^1$Total yield (%) of 1HOD and 3HOD based on 1,3-butadiene charged.
*$^2$Amount (%) of 1HOD to the total amount of 1HOD and 3HOD.
*$^3$Yield (%) of 1HHDT based on 1,3-butadiene charged.

EXAMPLE 45-3

In Example 2, the amount of palladium acetate was changed to 0.132 mmol, the amount of the phosphonite was changed to 1.99 mmol, 3 ml of triethylamine was used in addition to acetone as the solvent for reaction, the reaction temperature was changed to 75° C., the reaction time was changed to 30 minutes or one hour, and a small amount of the reaction solution was withdrawn from the reactor and analyzed.

| Examples | HOD yield (%)*1 | 1-HOD selectivity (%)*2 | 1-HHDT yield (%)*3 |
|---|---|---|---|
| 30 Minutes | 16.7 | 76.5 | 0.1 |
| 1 Hour | 42.5 | 78.5 | 0.2 |

*1Total yield (%) of 1HOD and 3HOD based on 1,3-butadiene charged.
*2Amount (%) of 1HOD to the total amount of 1HOD and 3HOD.
*3Yield (%) of 1HHDT based on 1,3-butadiene charged.

EXAMPLE 46

In Example 16, a phosphite was used instead of the phosphonite.

The reaction was carried out in the same manner as in Example 16, except that the amount of palladium acetate was changed to 0.098 mmol, 1.51 mmol of tris(2,5-di-t-butylnaphthyl)phosphite was used as the phosphite, 1.35 ml of triethylamine was used in addition to acetone as the solvent for reaction, the reaction temperature was changed to 90° C., and the reaction time was changed to 30 minutes. The results are shown in Table 5.

EXAMPLE 47

In Example 16, a phosphite was used instead of the phosphonite.

The reaction was carried out in the same manner as in Example 16, except that the amount of palladium acetate was changed to 0.098 mmol, 0.38 mmol of tris(2,5-di-t-butylnaphthyl)phosphite was used as the phosphite, 1.35 ml of triethylamine was used in addition to acetone as the solvent for reaction, the reaction temperature was changed to 90° C., and the reaction time was changed to one hour. The results are shown in Table 5.

EXAMPLE 48

In Example 2, a phosphinite was used instead of the phosphonite.

The reaction was carried out in the same manner as in Example 2, except that the amount of palladium acetate was changed to 0.062 mmol, 2.02 mmol of diphenyl(2,6-di-t-butylphenyl)phosphine was used as the phosphinite, the reaction temperature was changed to 90° C., and the reaction time was changed to one hour. The results are shown in Table 5.

EXAMPLE 49

The reaction was carried out in the same manner as in Example 2, except that the amount of palladium acetate was changed to 0.127 mmol, the phosphonite was changed to 2.01 mmol of benzyl(2,2'-methylenebis(4-methyl-6-t-butylphenoxy))phosphine, 3 ml of triethylamine was used in addition to acetone as the solvent for reaction, and the reaction was carried out for 6 hours. The results are shown in Table 5.

EXAMPLE 50

The reaction was carried out in the same manner as in Example 2, except that the amount of palladium acetate was changed to 0.127 mmol, the phosphonite was changed to 2.00 mmol of cyclohexylmethyl(2,2'-methylenebis(4-methyl-6-t-butylphenoxy))phosphine, and 3 ml of triethylamine was used in addition to acetone as the solvent for reaction. The results are shown in Table 5.

TABLE 5

| Examples | HOD yield (%)*1 | 1-HOD selectivity (%)*2 | 1-HHDT yield (%)*3 |
|---|---|---|---|
| 46 | 6.8 | 67.2 | 0.04 |
| 47 | 13.5 | 71.3 | 0.85 |
| 48 | 18.2 | 42.9 | 0.00 |
| 49 | 76.7 | 92.2 | 0.1 |
| 50 | 71.6 | 93.2 | 0.1 |

*1Total yield (%) of 1HOD and 3HOD based on 1,3-butadiene charged.
*2Amount (%) of 1HOD to the total amount of 1HOD and 3HOD.
*3Yield (%) of 1HHDT based on 1,3-butadiene charged.

EXAMPLE 51

The reaction and the distillation of the reaction solution were carried out in the same manner as in Example 1, except that the scale was enlarged five times using a stainless steel autoclave having an internal capacity of 1 l, to obtain 103 g of 1HOD, and the obtained 1HOD was subjected to a hydrogenation reaction.

Into a microautoclave of a shaking type having an internal capacity of 100 ml, 3.9 g of a catalyst having 13.7% of nickel and 1.9% of chromium supported on diatomaceous earth, and 26.0 g of 1HOD were charged, and the hydrogenation reaction was carried out under a hydrogen pressure of 40 kg/cm$^3$ at a reaction temperature of 120° C. for 2 hours. The reaction solution was analyzed by gas chromatography, whereby it was found that the hydrogenation reaction proceeded substantially quantitatively, the yield of n-octanol was at least 99%, and trace amounts of 2-octen-1-ol and n-octylaldehyde were detected.

EXAMPLE 52

Hydrogenation of HOD

In Example 51, the hydrogenation reaction was carried out under a hydrogen pressure of 20 kg/cm$^3$ for from 3.5 hours. The reaction solution was analyzed by gas chromatography, whereby the yield of n-octanol was 66.7%, the yield of 2-octen-1-ol was 26.4%, and the yield of n-octylaldehyde was 5.0%.

REFERENCE EXAMPLE 1

Preparation of (2,2'-methylenebis(4-methyl-6-t-butylphenoxy))phosphinochloride

Into a two-necked flask having an internal capacity of 1 l, 14.76 g (107.5 mmol) of phosphorus trichloride and 100 ml of toluene were charged under a nitrogen atmosphere and stirred by a magnetic stirrer. Then, a solution having 36.6 g (107.5 mmol) of 2,2'-methylenebis(4-methyl-6-t-butylphenol) and 25 ml of triethylamine dissolved in 180 ml of toluene, was dropwise added thereto over a period of 15 minutes under a nitrogen atmosphere. After completion of the addition, the reaction mixture was heated to 60° C. and stirred for one hour at that temperature. The reaction mixture was cooled to room temperature, and precipitated inorganic salts were filtered off. From the obtained filtrate, the solvent was distilled off, and the residue was dried under reduced pressure to obtain 43.07 g (106.3 mmol) of a white powder. By NMR, this powder was confirmed to be the desired product.

$^{31}$PNMR (CDCl$_3$, triphenyl phosphate: −18 ppm base) δ154.6 ppm $^1$HNMR (CDCl$_3$, (CH$_3$)$_4$Si base) δ/ppm
1.39(s, 18H, —C(CH$_3$)$_3$)
2.30(s, 6H, —CH$_3$)
3.71(d, J=12.0 Hz, 1H, ArCH$_2$Ar)
3.99(d, J=12.0 Hz, 1H, ArCH$_2$Ar)
7.03(s, 2H, —OArH)
7.09(s, 2H, —OArH)

EXAMPLE 53

Preparation of a branched alkyl phosphonite of the formula (8)

Preparation of benzyl(2,2'-methylenebis(4-methyl-6-t-butylphenoxy))phosphine

Into a two-necked flask having an internal capacity of 200 ml, 0.385 g (15.8 mmol) of flaky magnesium and 20 ml of THF were charged under a nitrogen atmosphere and stirred by a magnetic stirrer. Then, a solution having 2.68 g (15.7 mmol) of α-bromotoluene dissolved in 20 ml of THF, was dropwise added thereto over a period of 30 minutes under a nitrogen atmosphere. After completion of the addition, the reaction mixture was stirred under a heating and refluxing condition for one hour to obtain a Grignard reagent. This solution was cooled, and a solution having 6.33 g (15.6 mmol) of (2,2'-methylenebis(4-methyl-6-t-butylphenoxy)) phosphinochloride prepared in Reference Example 1 dissolved in 30 ml of THF, was dropwise added thereto over a period of 20 minutes with cooling in an ice bath. After completion of the addition, the reaction mixture was stirred under a heating and refluxing condition for one hour. Then, the THF solvent was distilled off under atmospheric pressure. The residue was dissolved in 100 ml of toluene, and insoluble inorganic salts were removed by filtration. This toluene solution was subjected to distillation under reduced pressure to distill off toluene and to obtain a crude phosphonite. The product was recrystallized from acetonitrile to obtain 3.77 g of a white powder. By NMR, this powder was confirmed to be the desired product. $^{31}$PNMR (CDCl$_3$, triphenyl phosphate: −18 ppm base) δ182.4 ppm $^1$HNMR (CDCl$_3$, (CH$_3$)$_4$Si base) δ/ppm
1.24(s, 18H, —C(CH$_3$)$_3$)
2.25(s, 6H, —CH$_3$)
3.26(dd, J=12.6, 4.2 Hz, 1H, ArCH$_2$Ar)
3.57(m, 2H, ArCH$_2$P)
4.22(d, J=12.6 Hz, 1H, ArCH$_2$Ar)
6.94(s, 2H, —OArH)
7.08(s, 2H, —OArH)
7.2–7.4(m, 5H, —ArH)

EXAMPLE 54

Preparation of a branched alkyl phosphonite of the formula (8)

Preparation of cyclohexylmethyl(2,2'-methylenebis (4-methyl-6-t-butylphenoxy))phosphine Into a two-necked flask having an internal capacity of 200 ml, 0.488 g (20.1 mmol) of flaky magnesium and 25 ml of THF were charged under a nitrogen atmosphere and stirred by a magnetic stirrer. Then, a solution having 3.56 g (20.1 mmol) of cyclohexylmethyl bromide dissolved in 25 ml of THF, was dropwise added thereto over a period of 30 minutes under a nitrogen atmosphere. After completion of the addition, the reaction mixture was stirred under a heating and refluxing condition for one hour to obtain a Grignard reagent. This solution was cooled, and a solution having 8.09 g (20.0 mmol) of (2,2'-methylenebis(4-methyl-6-t-butylphenoxy))phosphinochloride prepared in Reference Example 1 dissolved in 30 ml of THF, was dropwise added thereto over a period of 20 minutes with cooling in an ice bath. After completion of the addition, the reaction mixture was stirred under a heating and refluxing condition for one hour. Then, the THF solvent was distilled off under atmospheric pressure, and the residue was dissolved in 120 ml of toluene. Insoluble inorganic salts were removed by filtration. This toluene solution was subjected to distillation under reduced pressure to distill off toluene and to obtain a crude phosphonite. The product was recrystallized from acetonitrile to obtain 4.97 g of a white powder. By NMR, the powder was confirmed to be the desired product.

$^{31}$PNMR (CDCl$_3$, triphenyl phosphate: −18 ppm base) δ192.9 ppm $^1$HNMR (CDCl$_3$, (CH$_3$)$_4$Si base) δ/ppm
1.0–2.3(13H, —CH$_2$C$_6$H$_{11}$)
1.33(s, 18H, —C(CH$_3$)$_3$)
2.23(s, 6H, —CH$_3$)
3.27(d, J=12.6 Hz, 1H, ArCH$_2$Ar)
4.28(d, J=12.6 Hz, 1H, ArCH$_2$Ar)
6.93(s, 2H, —OArH)
7.07(s, 2H, —OArH)

REFERENCE EXAMPLE 2

Preparation of (2-hydroxy-3-t-butyl-5-methylphenyl)-(2-hydroxy-4-t-butylphenyl)methane In a 300 ml eggplant type flask equipped with a Dimroth condenser, 33.6 g (0.22 mol) of 3-t-butylphenol was suspended in 30 ml of water. To this suspension, an aqueous solution having 12.6 g (0.32 mol) of sodium hydroxide dissolved in 30 ml of water, was added, and 35 ml of a 37% formaldehyde aqueous solution (0.47 mol of formaldehyde) was further added. The mixture was stirred by a magnetic stirrer. This mixture was heated to 80° C. and stirred at that temperature for 8 hours. The reaction mixture was cooled to room temperature and acidified by concentrated hydrochloric acid, and then extracted with ethyl acetate. The obtained ethyl acetate solution was washed with water and dried over anhydrous magnesium sulfate. The anhydrous magnesium sulfate was removed, and from the solution thereby obtained, ethyl acetate was distilled off. The residue thereby obtained was suspended and washed with n-hexane to obtain 20.9 g (0.12 mol, yield: 51.7%) of intermediate 2-(hydroxymethyl)-5-t-butylphenol as a white powder. By $^1$HNMR, this powder was confirmed to be the desired product.

$^1$HNMR (CDCl$_3$, (CH$_3$)$_4$Si base) δ/ppm
1.29(s, 9H, —C(CH$_3$)$_3$)
2.33(br.s, 1H, —CH$_2$OH)
4.82(s, 2H, —CH$_2$OH)
6.88(dd, J=7.8, 1.8 Hz, 1H, ArH p-position to OH)
6.93(d, J=1.5 Hz, 1H, ArH m-position to OH)
6.96(d, J=7.8 Hz, 1H, ArH o-position to OH)
7.23(br.s, 1H, ArOH)

In a 300 ml eggplant-type flask equipped with a Dimroth condenser, 10.3 g (0.057 mol) of intermediate 2-(hydroxymethyl)-5-t-butylphenol and 10.2 g (0.062 mol) of 2-t-butyl-4-methylphenol were suspended in 60 ml of water. To this suspension, an aqueous solution having 10.2 g (0.26 mol) of sodium hydroxide dissolved in 50 ml of water, was added, and the mixture was stirred by a magnetic stirrer. This mixture was heated to a temperature of from 100° to 110° C. and stirred at that temperature for 17.5 hours. The reaction mixture was cooled to room temperature, acidified by concentrated hydrochloric acid and then extracted with ethyl acetate. The obtained ethyl acetate solution was washed with water and then dried over anhydrous magnesium sulfate. From the solution having the anhydrous magnesium sulfate removed, ethyl acetate was distilled off, and the obtained residue was roughly separated by silica gel column chromatography. To the obtained brown highly viscous oil, n-hexane was added and left to stand still to obtain 6.7 g (0.021 mol, yield: 36.0%) of (2-hydroxy-3-t-butyl-5-methylphenyl)-(2-hydroxy-4-t-butylphenyl) methane as a white solid. By 1HNMR, this solid was confirmed to be the desired product.

$^1$HNMR (CDCl$_3$, (CH$_3$)$_4$Si base) δ/ppm
1.25(s, 9H, —C(CH$_3$)$_3$)
1.39(s, 9H, —C(CH$_3$)$_3$)
2.24(s, 3H, —CH$_3$)
3.86(s, 2H, ArCH$_2$Ar)
5.65(S, 1H, —OH)
6.42(S, 1H, —OH)
6.77(d, J=1.8 Hz, 1H, ArH)
6.92(dd, J=8.1, 1.8 Hz, 1H, ArH)
6.95(d, J=2.4 Hz, 2H, ArH)
7.20(d, J=8.1 Hz, 1H, ArH)

EXAMPLE 55

Preparation of 5-methyl-3,5'-di-t-butyldiphenylmethane-2,2'-dioxy)phosphine

In a 200 ml four-necked flask equipped with a Dimroth condenser and a 50 ml dropping funnel, 3.05 g (9.4 mmol) of (2-hydroxy-3-t-butyl-5-methylphenyl)-(2-hydroxy-4-t-butylphenyl)methane obtained in Reference Example 2 and 3.1 ml of triethylamine were dissolved in 30 ml of toluene under a nitrogen atmosphere. To this solution, a solution having 1.27 ml (9.4 mmol) of dichlorophenylphosphine dissolved in 20 ml of toluene, was added from the dropping funnel over a period of 25 minutes at room temperature with stirring by a magnetic stirrer. After completion of the addition, the reaction mixture was heated to 60° C. and stirred at that temperature for one hour. The reaction mixture was cooled to room temperature, and precipitated inorganic salts were filtered off. From the obtained filtrate, the solvent was distilled off. The obtained residue was separated by silica gel column chromatography, and the solvent was distilled off to obtain 1.97 g (4.6 mmol, yield: 48.8%) of a white powder. From $^{31}$PNMR and $^1$HNMR, this powder was confirmed to be the desired product.

$^{31}$PNMR (CDCl$_3$, triphenyl phosphate: −18 ppm base) δ164.5 ppm $^1$HNMR (CDCl$_3$, (CH$_3$)$_4$Si base) δ/ppm
1.25(s, 9H, —C(CH$_3$)$_3$)
1.27(s, 9H, —C(CH$_3$)$_3$)
2.29(s, 3H, —CH$_3$)
3.45(d, J=12.9 Hz, 1H, ArCH$_2$Ar)
4.50(dd, J=12.6, 3.3 Hz, 1H, ArCH$_2$Ar)
7.01(s, 2H, —OArH)
7.06–7.14(s, 3H, —OArH)
7.5–7.6(m, 3H, PArH m, o-position)
8.0–8.12(m, 2H, PArH o-position)

REFERENCE EXAMPLE 3

Preparation of (2-hydroxy-3-t-butyl-5-methylphenyl)-(2-hydroxy-3,5-dimethylphenyl)methane In a 300 ml eggplant-type flask equipped with a Dimroth condenser, 25.0 g (0.20 mol) of 2,4-dimethylphenol was suspended in 50 ml of water. To this suspension, an aqueous solution having 10.0 g (0.25 mol) of sodium hydroxide dissolved in 50 ml of water, was added, and 46 ml of 37% formaldehyde (0.61 mol of formaldehyde) was further added. The mixture was stirred by a magnetic stirrer. This mixture was heated to 70° C. and stirred at that temperature for 2 hours. The reaction mixture was cooled to room temperature, then acidified by concentrated hydrochloric acid and extracted with ethyl acetate. The obtained ethyl acetate solution was washed with water and then dried over anhydrous magnesium sulfate. From the solution having the anhydrous magnesium sulfate removed, ethyl acetate was distilled off. The obtained residue was separated from silica gel column chromatography, and the solvent was distilled off, followed by suspension washing with n-hexane to obtain 20.5 g (0.13 mol, yield: 65.9%) of intermediate 6-(hydroxymethyl)-2,4-dimethylphenol as a white powder. By $^1$HNMR, the powder was confirmed to be the desired product.

$^1$HNMR (CDCl$_3$, (CH$_3$)$_4$Si base) δ/ppm
2.20(s, 3H, —CH$_3$)
2.21(s, 3H, —CH$_3$)
2.50(br.s, 1H, —CH$_2$OH)
4.74(s, 2H, —CH$_2$OH)
6.64(s, 1H, ArH)
6.88(s, 1H, ArH)
7.17(s, 1H, ArOH)

In a 300 ml eggplant-type flask equipped with a Dimroth condenser, 10.4 g (0.068 mol) of intermediate 6-(hydroxymethyl)-2,4-dimethylphenol and 11.6 g (0.071 mol) of 2-t-butyl-4-methylphenol were suspended in 50 ml of water. To this suspension, an aqueous solution having 10.3 g (0.26 mol) of sodium hydroxide dissolved in 50 ml of water, was added, and the mixture was stirred by a magnetic stirrer. This mixture was heated to 100° C. and stirred at that temperature for 12 hours. The reaction mixture was cooled to room temperature, then acidified by concentrated hydrochloric acid and extracted with toluene. The obtained toluene solution was washed with water and then dried over anhydrous magnesium sulfate. From the solution having the anhydrous magnesium sulfate removed, toluene was distilled off, and the obtained residue was separated by silica gel chromatography to obtain 10.6 g (0.036 mol, yield: 51.9%) of (2-hydroxy-3-t-butyl-5-methylphenyl)-(2-hydroxy-3,5-dimethylphenyl)methane as a brown highly viscous liquid. By $^1$HNMR, the liquid was confirmed to be the desired product.

$^1$HNMR (CDCl$_3$, (CH$_3$)$_4$Si base) δ/ppm
1.39(s, 9H, —C(CH$_3$)$_3$)
2.20(s, 3H, —CH$_3$)
2.22(s, 3H, —CH$_3$)
2.25(s, 3H, —CH$_3$)
3.85(S, 2H, ArCH$_2$Ar)
5.36(s, 1H, —OH)
6.34(s, 1H, —OH)
6.80(s, 1H, ArH)
6.95(s, 3H, ArH)

EXAMPLE 56

Preparation of 5,3'5'-trimethyl-3-t-butyldiphenylmethane-2,2'-dioxy)phosphine

In a 200 ml four-necked flask equipped with a Dimroth condenser and a 50 ml dropping funnel, 10.4 g (35.0 mmol) of (2-hydroxy-3-t-butyl-5-methylphenyl)-(2-hydroxy-2,4-dimethylphenyl)methane obtained in Reference Example 3 and 11.5 ml of triethylamine were dissolved in 40 ml of toluene under a nitrogen atmosphere. To this solution, a solution having 4.75 ml (35.0 mmol) of dichlorophenylphosphine dissolved in 40 ml of toluene, was added by the dropping funnel over a period of 30 minutes at room temperature with stirring by a magnetic stirrer. After completion of the addition, the reaction mixture was heated to 60° C. and stirred at that temperature for one hour. The reaction mixture was cooled to room temperature, precipitated inorganic salts were filtered off. From the obtained filtrate, the solvent was distilled off. The obtained residue was separated by silica gel column chromatography, and the solvent was distilled off to obtain 10.3 g (25.5 mmol, yield: 73.0%) of a white powder. From $^{31}$PNMR and $^1$HNMR, this powder was confirmed-to be the desired product.

$^{31}$PNMR (CDCl$_3$, triphenyl phosphate: −18 ppm base) δ163.1 ppm $^1$HNMR (CDCl$_3$, (CH$_3$)$_4$Si base) δ/ppm
1.28(s, 9H, —C(CH$_3$)$_3$)
2.17(s, 3H, —CH$_3$)
2.27(s, 3H, —CH$_3$)
2.29(s, 3H, —CH$_3$)
3.39(d, J=12.6 Hz, 1H, ArCH$_2$Ar)
4.50(dd, J=12.6, 3.6 Hz, 1H, ArCH$_2$Ar)
6.85(s, 1H, —OArH)
7.00(d, J=2.1 Hz, 1H, —OArH)
7.08(d, J=1.5 Hz, 1H, —OArH)
7.11(d, J=1.8 Hz, 1H, —OArH)
7.50–7.62(m, 3H, PArH m, p-position)
7.97–8.12(m, 2H, PArH o-position)

EXAMPLE 57

Reaction of

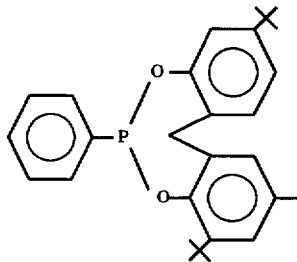

The reaction was carried out in the same manner as in Example 16, except that the amount of palladium acetate was changed to 0.192 mmol, the phosphonite was changed to 1.54 mmol of 5-methyl-3,5'-di-t-butyldiphenylmethane-2,2'-dioxy)phosphine, 2.65 ml of triethylamine was used in addition to acetone as the solvent for reaction, and the reaction time was changed to 30 minutes. The results are shown in Table 6.

TABLE 6

| Examples | HOD yield (%)*1 | 1-HOD selectivity (%)*2 | 1-HHDT yield (%) *3 |
|---|---|---|---|
| 57 | 10.3 | 63.9 | 0.1 |

*1Total yield (%) of 1HOD and 3HOD based on 1,3-butadiene charged.
*2Amount (%) of 1HOD to the total amount of 1HOD and 3HOD.
*3Yield (%) of 1HHDT based on 1,3-butadiene charged.

What is claimed is:
1. A phosphonite compound of the formula (7):

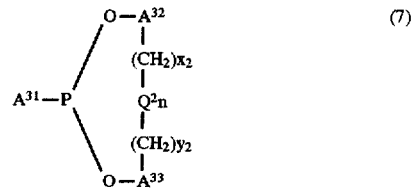

wherein $A^{31}$ is an aryl group or an alkyl group, which may be substituted, provided that the alkyl groups has no branch at the β-position, each of $A^{32}$ and $A^{33}$ is an arylene group having an alkyl substituent and $A^{32}$ and $A^{33}$ are not the same, each of $x^2$ and $y^2$ which are independent of each other, is an integer of 0 or 1, $Q^2$ is a bivalent linking group of the formula —CR$^{41}$R$^{42}$—, —O—, —S—, SO$_2$—, —NR$^{43}$—, —SiR$^{44}$R$^{45}$— or —CO—, each of $R^{41}$ and $R^{42}$ which are independent of each other, is hydrogen, a C$_{1-12}$ alkyl group, a phenyl group, a tolyl group or an anisyl group, and each of $R^{43}$, $R^{44}$ and $R^{45}$ which are independent of one another, is hydrogen or a methyl group, and n is an integer of from 0 to 1.

2. A phosphonite compound of the formula (8):

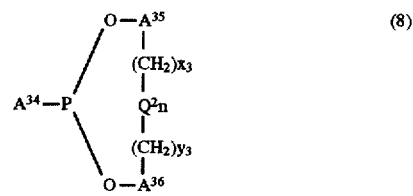

wherein $A^{34}$ is an alkyl group or an aralkyl group, which has a branch at the β-position, each of $A^{35}$ and $A^{36}$ which are independent of each other, is an arylene group which may be substituted, each of $x^3$ and $y^3$ which are independent of each other, is an integer of 0 or 1, $Q^2$ is a bivalent linking group of the formula —CR$^{46}$R$^{47}$—, —O—, —S—, —SO$_2$—, —NR$^{48}$—, —SiR$^{49}$R$^{50}$— or —CO—, each of $R^{46}$ and $R^{47}$ which are independent of each other, is hydrogen, a C$_{1-12}$ alkyl group, a phenyl group, a tolyl group or an anisyl group, each of $R^{48}$, $R^{49}$ and $R^{50}$ which are independent of one another, is hydrogen or a methyl group, and n is an integer of 0 or 1.

3. A compound selected from the group consisting of phenyl(5-methyl-3,5'-di-t-butyldiphenylmethane-2,2'-dioxy) phosphine and phenyl(5,3',5'-trimethyl-3-t-butyldiphenylmethane-2,2'-dioxy)phosphine.

4. A phosphonite compound of the formula (8):

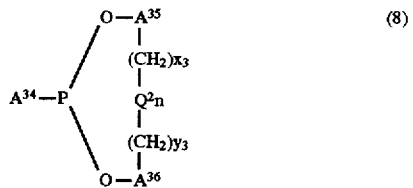

wherein $A^{34}$ is a cyclohexylmethyl group or benzyl group, each of $A^{35}$ and $A^{36}$ which are independent of each other, is an arylene group which may be substituted, each of $x^3$ and $y^3$ which are independent of each other, is an integer of 0 or 1, $Q^2$ is a bivalent linking group of the formula —CR$^{46}$R$^{47}$—, —O—, —S—, —SO$_2$—, —NR$^{48}$—, —SiR$^{49}$R$^{50}$— or —CO—, each of $R^{46}$ and $R^{47}$ which are independent of each other, is hydrogen, a C$_{1-12}$ alkyl group, a phenyl group, a tolyl group or an anisyl group, each $R^{48}$, $R^{49}$ and $R^{50}$ which are independent of one another, is hydrogen or a methyl group, and n is an integer of 0 or 1.

5. A bis(phosphonite)palladium complex comprising a phosphonite compound of the formula (1) or (2);

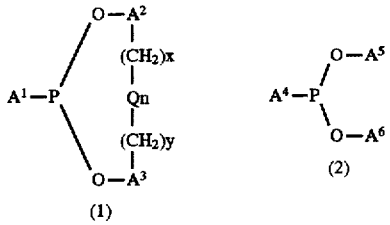

wherein each of $A^1$ and $A^4$, which are independent of each other, is an aryl group or an alkyl group, which may be substituted, each of $A^5$ and $A^6$, which are independent of one another, is an aryl group which may be substituted, each of $A^2$ and $A^3$, which are independent of one another, is an arylene group which may be substituted, each of x and y which are independent of one another, is an integer of 0 or 1, Q is a bivalent linking group of the formula —$CR^1R^2$—, —O—, —S—, —$SO_2$—, —$NR^3$—, —$SiR^4R^5$— or —CO—, each of $R^1$ and $R^2$ which are independent of each other, is hydrogen, a $C_{1-12}$ alkyl group, a phenyl group, a tolyl group or an anisyl group, each of $R^3$, $R^4$ and $R^5$, which are independent of one another, is hydrogen or a methyl group, and each of n, m and k, which are independent of one another, is an integer of 0 or 1.

6. The bis(phosphonite)palladium complex according to claim 5, wherein the complex comprises a phosphonite compound of the formula (1) in which $A^1$ is a $C_{6-30}$ aryl group and Q is —$CR^1R^2$—, wherein each of $R^1$ and $R^2$, which are independent of each other, is a hydrogen atom or a $C_{1-6}$ alkyl group and each of $A^2$ and $A^3$ is a 1,2-arylene group.

7. The bis(phosphonite)palladium complex according to claim 6, wherein each of $A^2$ and $A^3$ is a 1,2-phenylene group which may have as a substituent a $C_{1-20}$ alkyl group or a $C_{1-20}$ alkoxy group at the 6-position and as a substituent a $C_{1-20}$ alkyl group at one or more of the 3-, 4- and 5-positions.

8. The bis(phosphonite)palladium complex according to claim 5, wherein the complex comprises a phosphonite compound of the formula (2) in which $A^4$ is a $C_{6-20}$ aryl group and each of $A^5$ and $A^6$ is a phenyl group having a $C_{1-20}$ alkyl group at the o-position.

9. The bis(phosphonite)palladium complex according to claim 5, wherein $A^4$ is a $C_{6-30}$ alkyl group which may be substituted by a $C_{1-20}$ alkoxy group, a $C_{2-30}$ dialkylamino group or a group of the formula —$SO_3Na$, —COONa or —$COOCH_3$.

10. The bis(phosphonite)palladium complex according to claim 5, wherein $A^4$ is a $C_{6-30}$ aryl group which may be substituted by an alkyl group, an aryl group, an alkoxy group, a dialkylamino group or a group of the formula —$SO_3Na$.

* * * * *

UNITED STATES PATENT AND TRADEMARK OFFICE
CERTIFICATE OF CORRECTION

PATENT NO. : 5,712,403
DATED : January 27, 1998
INVENTOR(S) : Keiichi SATO, et al.

It is certified that error appears in the above-indentified patent and that said Letters Patent is hereby corrected as shown below:

On the title page, item [30] should be:

--[30]   Foreign Application Priority Data
   Jun. 29, 1994   [JP]   Japan  ............   6-147732--

Signed and Sealed this

Seventeenth Day of March, 1998

*Attest:*

BRUCE LEHMAN

*Attesting Officer*          Commissioner of Patents and Trademarks